(12) United States Patent
Nakano et al.

(10) Patent No.: US 6,613,588 B2
(45) Date of Patent: Sep. 2, 2003

(54) FLOATING PARTICLE INSPECTION METHOD AND ITS APPARATUS AND A SEMICONDUCTOR DEVICE PROCESSING APPARATUS

(75) Inventors: Hiroyuki Nakano, Yokohama (JP); Toshihiko Nakata, Hiratsuka (JP)

(73) Assignee: Hitachi, Ltd., Tokyo (JP)

( * ) Notice: Subject to any disclaimer, the term of this patent is extended or adjusted under 35 U.S.C. 154(b) by 128 days.

(21) Appl. No.: 09/933,185

(22) Filed: Aug. 21, 2001

(65) Prior Publication Data

US 2002/0006731 A1 Jan. 17, 2002

Related U.S. Application Data

(63) Continuation-in-part of application No. 09/260,074, filed on Mar. 2, 1999, now Pat. No. 6,355,570.

(51) Int. Cl.[7] ............................................. H01L 21/00
(52) U.S. Cl. ...................... 438/9; 156/345.24; 216/60; 438/710
(58) Field of Search ............... 438/9, 710; 156/345.24, 156/345.25, 345.26; 216/59, 60, 65, 67

(56) References Cited

U.S. PATENT DOCUMENTS 6,125,789 A * 10/2000 Gupta et al. ........ 156/345.24 X

FOREIGN PATENT DOCUMENTS

| JP | 57-118630 | 7/1982 |
| JP | 3-25355 | 2/1991 |
| JP | 3-147317 | 6/1991 |
| JP | 6-82358 | 3/1994 |
| JP | 6-124902 | 5/1994 |
| JP | 10-213539 | 8/1998 |

* cited by examiner

Primary Examiner—William A. Powell
(74) Attorney, Agent, or Firm—Antonelli, Terry, Stout & Kraus, LLP

(57) ABSTRACT

The present invention is to detect particles suspended in a processing chamber using a single observation window and an optical system formed as a single unit and to provide precise detection of very weak particle-scattered light. When a thin film is being formed on an object to be processed in a processing chamber or if such a thin film is being processed, an optical guide module guides a laser beam from a laser light source separated from a laser illumination/scattered light detection optical system. The laser beam is guided to the laser illumination/scattered light detection optical system. The processing chamber is illuminated by the laser illumination/scattered light detection optical system via an observation window. The illumination light is scattered by particles in the processing chamber. Back-scattered light passing through the observation window is detected by the laser illumination/scattered light detection optical system.

12 Claims, 21 Drawing Sheets

FLOATING PARTICLE INSPECTION METHOD AND ITS APPARATUS AND A SEMICONDUCTOR DEVICE PROCESSING APPARATUS

CROSS-REFERENCE TO RELATED APPLICATION

The present application is a continuation-in-part application of prior application U.S. Ser. No. 09/260,074, filed Mar. 2, 1999, now U.S. Pat. No. 6,335,570.

BACKGROUND OF THE INVENTION

The present invention relates to a method and apparatus for detecting fine particles suspended in a apparatus for producing semiconductor device such as semiconductor substrates and liquid crystal substrates, as well as a semiconductor device processing apparatus. More specifically, the present invention relates to a method and apparatus for performing in-situ measurements of particles suspended in a processing chamber (vacuum processing chamber) for performing processes such as thin-film deposition and etching.

Processes using plasma are widely used in semiconductor fabrication processes and liquid crystal display apparatus substrate fabrication processes, e.g., in etching apparatus.

FIG. 27 shows an example of a processing apparatus that uses plasma in the form of a parallel plate plasma etching apparatus. As shown in FIG. 27, this type of apparatus uses a high-frequency signal from a signal generator 83 to modulate the output potential from a power amp 84. This high-frequency potential is split up using a distributor 85 applied to an upper electrode 81 and a lower electrode 82 disposed parallel to each other in a processing chamber. Discharge between the two electrodes 81, 82 generates a plasma 71 from an etching gas. Etching is performed on the workpiece, e.g., a semiconductor substrate (wafer) W. The high-frequency signal can use, for example, a frequency of approximately 400 kHz.

In this plasma etching apparatus, it is known that the etching reaction product from the plasma operation is deposited on the wall surface of the plasma processing chamber or the electrodes. As time goes by, the product peels off and forms suspended fine particles. As soon as the etching operation is completed and the plasma discharge stops, these suspended fine particles drop onto the wafer to form adhered particles, leading to negative circuit properties and visual pattern defects. Ultimately, these can lead to reduced yield and reduced reliability of the elements.

Many types of apparatus for inspecting particles adhered to the surface of the wafer have been proposed and implemented, but these remove the wafer from the plasma processing apparatus to perform inspection. By the time it is known that many particles are present, the processing of another wafer is already begun. This leads to clusters of defects and reduced yield. Also, evaluations performed after processing cannot determine distribution or changes over time in particles inside the processing.

Thus, there is a need in the field of semiconductor fabrication, liquid crystal fabrication, and the like of a technology for performing in-situ real-time monitoring of contamination status in processing chambers.

The sizes of fine particles suspended in the processing chamber range from submicrons to several hundred microns. In the semiconductor field, where integration scale is growing to include 256 Mbit DRAMs (Dynamic Random Access Memory) and 1 Gbit DRAMs, the minimum circuit pattern widths is decreasing to 0.25–0.18 microns. Thus, there is a need to detect sizes of particles down to the order of submicrons.

Conventional technologies for monitoring fine particles suspended in processing chambers (vacuum processing chambers) such as plasma processing chambers include Japanese laid-open patent publication number Sho 57-118630 (background technology 1), Japanese laid-open patent publication number Hei 3-25355 (background technology 2), Japanese laid-open patent publication number Hei 3-147317 (background technology 3), Japanese laid-open patent publication number Hei 6-82358 (background technology 4), Japanese laid-open patent publication number Hei 6-124902 (background technology 5), and Japanese laid-open patent publication number Hei 10-213539 (background technology 6).

The background technology 1 discloses a vaporization apparatus equipped with: means for illuminating a reaction space with a parallel light having a spectrum different from the spectrum of self-emitted light of the reaction space; and means for receiving parallel light illumination and detecting light scattered by fine particles generated in the reaction space.

The background technology 2 discloses a apparatus for measuring fine particles that uses scattering of laser light to measure fine particles adhered to a semiconductor substrate surface and suspended fine particles. The apparatus for measuring fine particles is equipped with a laser light phase modulator generating two laser lights modulated at predetermined frequencies having identical wavelengths and mutual phase differences; an optical system intersecting the two laser lights in a space containing the fine particles to be measured; an optical detection system receiving light scattered by the fine particles to be measured in the region where the two laser lights intersect and converting the light into an electrical signal; and a signal processor extracting a signal component from the electrical signal generated by the scattered light where the frequency is identical or twice the frequency of a phase modulation signal from the laser light phase modulator and the phase difference with the phase modulation signal is constant in time.

The background technology 3 discloses a technology for measuring contamination status in a reaction container that includes a step for performing scanning illumination with coherent light and generating scattered light in the reaction container and a step for detecting the scattered light in the reaction container. The scattered light is analyzed to measure the contamination status.

The background technology 4 discloses a particle detector equipped with: laser means generating a laser light; scanner means using the laser light to scan a region in a reaction chamber of a plasma processing tool containing particles to be measured; a video camera generating a video signal of laser light scattered by particles in the region; and means for processing and displaying an image from the video signal.

The background technology 5 discloses a plasma processing apparatus equipped with: a camera apparatus observing a plasma generating region in a plasma processing chamber; a data processing module processing an image obtained from the camera apparatus to obtain desired information; and a control module controlling at least one of the following list to reduce particles based on information obtained by the data processing module: evacuating means; process gas introducing means; high-frequency potential applying means; and purge gas introducing means.

The background technology 6 discloses a fine particle sensor including: a light emitter sending out a light beam illuminating a space to be measured; a detector containing an optical detector and an optical system focusing the scattered light from the space to be measured and directing it to the optical detector, the being set up so that the optical detector generates a signal representing the intensity of the light directed toward the optical detector; a pulse detector connected to the optical detector to analyze the signal from the optical detector, and detecting pulses in the signal from the optical detector; and signal processing means containing an event detector detecting a series of pulses resulting from scattered light generated by fine particles accompanying multiple illuminations by the beam while it moves in the measurement space.

In the conventional technologies described above, a laser light is sent in through an observation window disposed on a side surface of a processing apparatus. A different observation window from the laser entry observation window is disposed on the facing surface or another side surface to allow detection of front-scattering or side-scattering of the laser. Thus, in these systems for detecting front-scattered light and side-scattered light, the illumination optical system and the detection optical system are formed as different units and two observation windows are needed to attach these. Also, optical axis adjustments and the like need to be performed for both the illumination and detection optical systems, making operation difficult.

Also, an observation window is almost always disposed on the side surface of a plasma processing chamber to allow monitoring of plasma emission and the like, but in many cases only one observation window is provided. Thus, the conventional methods that require two observation windows cannot be implemented for fabrication apparatus with a processing chamber that only has one observation window.

Furthermore, in conventional systems that detect front-scattered light and side-scattered light, the illumination beam sent into the processing chamber is rotationally scanned. Observation of fine particle generation over the entire surface of the workpiece such as a wafer requires multiple observation windows and detection optical systems, leading to significant cost increases. Also, providing multiple observation windows and detection optical systems is extremely difficult practically due to space factor restrictions.

In the semiconductor field, where integration is proceeding to the levels of 256 Mbit DRAMs and 1 Gbit DRAMs, the minimum circuit pattern width is being reduced down to 0.25–0.18 microns, creating the need to detect particles with sizes on the order of submicrons. However, with the conventional technologies, separating light scattered by fine particles from plasma emission is difficult, so these technologies have been restricted to use in measuring relatively large fine particles, while detection of fine particles with sizes on the order of submicrons is difficult.

SUMMARY OF THE INVENTION

In the present invention, an illumination optical system and a detection optical system share the use of a single observation window. An optical system formed as a single unit detects particles suspended in a processing chamber. Also, the present invention provides a method and apparatus for forming a compact illumination/detection optical system that can be attached in a limited, small space. Also, the present invention provides a highly reliable method and apparatus for precisely detecting very weak particle-scattered light. Also, the present invention provides a method and apparatus for determining particle generation over the entire surface of a body being processed, e.g., a wafer.

According to another aspect of the present invention, when a desired film-forming/processing operation is being performed on a body being processed in a processing chamber, a laser light guided by an optical fiber from an external laser light source is passed through an observation window and illuminates the inside of the processing chamber. Back-scattered light scattered by particles in the processing chamber passes through the same observation window and is received by a detection optical system. The detection signal transferred to the processing module through an optical fiber is used to determine the quantity, sizes, and distribution of the particles. The results of this are displayed on a display.

According to another aspect of the present invention, the illumination beam illuminating inside the processing chamber through the observation window is rotationally scanned horizontally and back-scattered light generated in the processing chamber is detected so that a two-dimensional distribution of particles is determined.

According to another aspect of the present invention, the illumination beam illuminating inside the processing chamber through the observation window is split into multiple beams. These multiple beams are sequentially or simultaneously illuminated and the backscattered light thereof are detected so that a two-dimensional distribution of particles is determined.

These and other objects, features and advantages of the invention will be apparent from the following more particular description of preferred embodiments of the invention, as illustrated in the accompanying drawings.

DESCRIPTION OF THE PREFERRED EMBODIMENTS

The following is a description of the embodiments of the present invention using FIG. 1 through FIG. 26.

The embodiments of the present invention described below demonstrate implementations for parallel plate plasma etching apparatus used in plasma dry etching apparatus. However, the scope of the present invention is not restricted to this, and can be implemented for thin-film deposition apparatus, e.g., sputtering apparatus and CVD apparatus, and thin-film deposition/processing apparatus, e.g., ECR etching apparatus, microwave etching apparatus, and ashing apparatus.

First Embodiment

Figure 1:
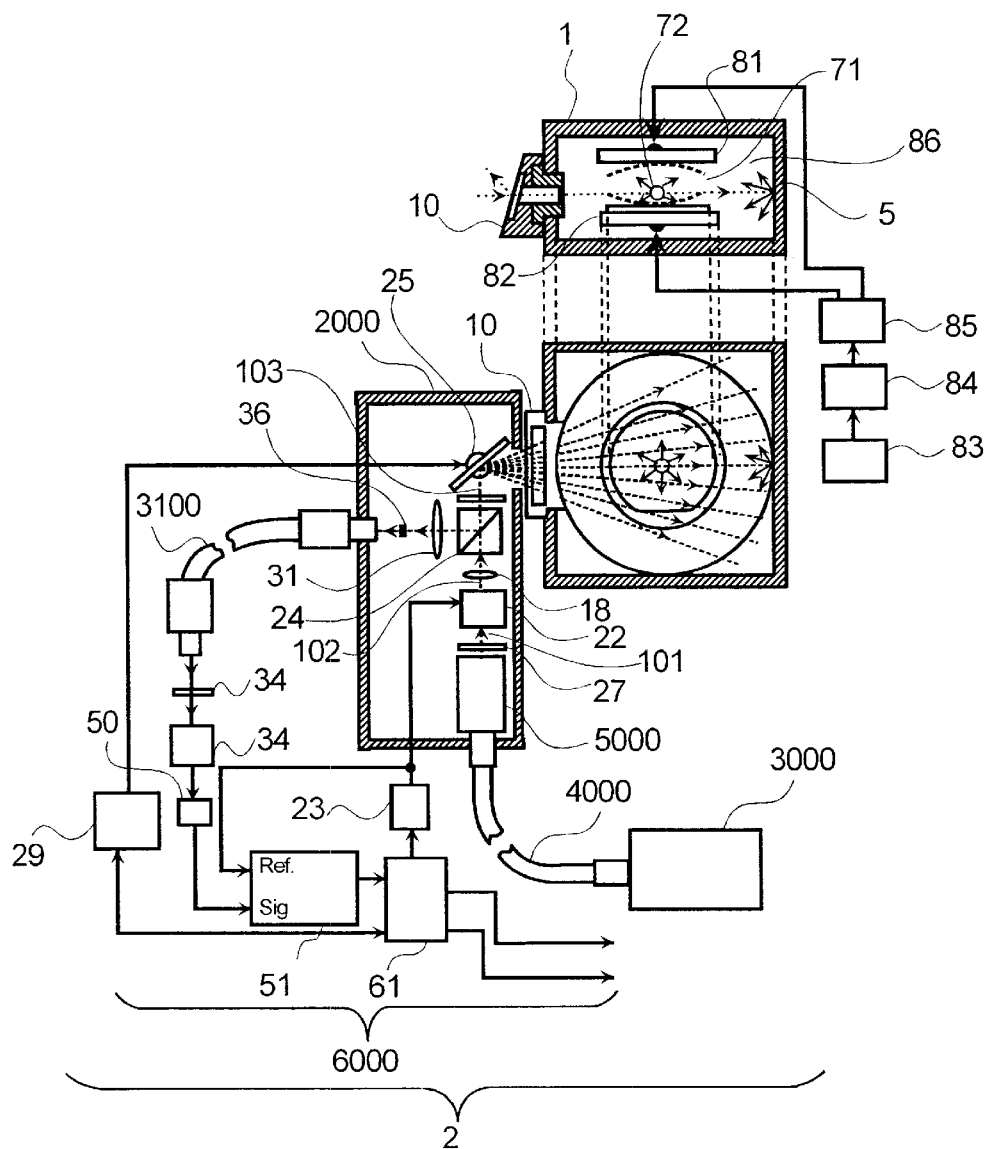
FIG. 1 is a drawing showing the architecture of an etching processing apparatus equipped with a apparatus for measuring particles suspended in plasma according to a first embodiment of the present invention.

First, a plasma etching apparatus according to a first embodiment of the present invention will be described using FIG. 1 through FIG. 10. FIG. 1 shows the architecture of an etching processing apparatus equipped with a apparatus for measuring particles floating in plasma.

As shown in FIG. 1, an etching processing apparatus 1 uses a high-frequency signal from the signal generator 83 to modulate the output voltage from the power amp 84. This high-frequency voltage is distributed by the distributor 85 and applied to the upper electrode 81 and the lower electrode 82 oriented parallel to each other in the plasma processing chamber 86. The discharge between these electrodes generates the plasma 71 from the etching gas, resulting in the etching of the semiconductor substrate (wafer) 72, which serves as the activation seed and the object of processing. The high-frequency signal can be, for example, a signal with a frequency of 400 kHz.

A plasma-suspended particle measuring apparatus 2 is formed primarily from a laser illumination/scattered light detection optical system 2000 and a control/signal processing system 6000. The illumination exit/detection light entry section of the laser illumination/scattered light detection optical system 2000 is positioned so that it faces the observation window 10 disposed on a side surface of the plasma processing chamber 86.

Figure 6:
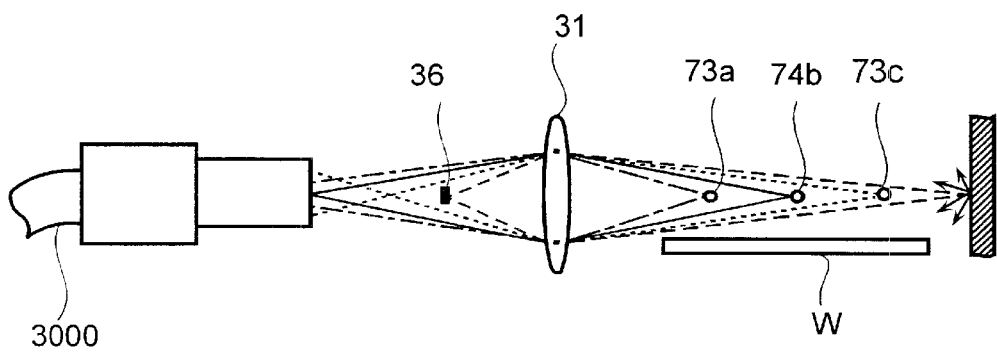
FIG. 6 is a simplified drawing of an optical system uses to detect light scattered by particles according to a first embodiment of the present invention.

A laser light is sent into the plasma processing chamber 86. The intensity of the light scattered by a particle in the plasma processing chamber 86 is inversely proportional to the square of the wavelength of the illumination laser (if the particle diameter and the laser wavelength are of the same order) and proportional to the intensity of the illumination laser. Also, it would be desirable for the laser light source to be compact so that the plasma-suspended particle measuring apparatus can be compact. Currently marketed laser light sources that are both compact and have a short wavelength includes, for example, a solid-state laser with excitation light from a semiconductor laser 3000 (e.g., 532 nm wavelength and output about 500 mW), as shown in FIG. 6. However, with many solid-state lasers with integrated excitation light sources, the excitation light source (semiconductor laser) and its optical elements may be small but the heat sink used to dissipate heat from the excitation light source can be big. This makes forming a compact plasma-suspended particle measuring apparatus difficult.

In this embodiment, the semiconductor laser 3000 and a wavelength converter 5000 from the solid-state laser with integrated excitation light source described above are separated, as shown in FIG. 3. The wavelength converter 5000 is installed in the plasma-suspended particle measuring apparatus 2 to provide a compact plasma-suspended particle measuring apparatus.

Figure 4:
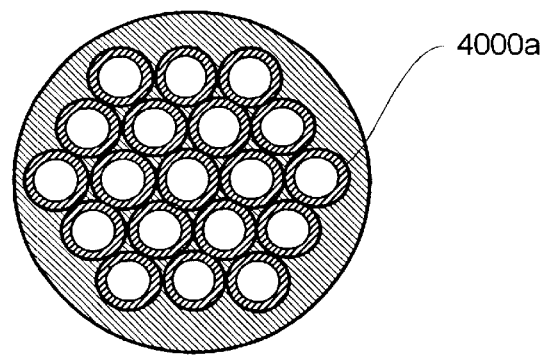
FIG. 4 is a cross-section drawing of a bundled fiber.

First, laser light from the semiconductor laser 3000 (e.g., a semiconductor laser with a wavelength of 809 nm) is guided by an optical fiber 4000 to the laser illumination/scattered light detection optical system 2000. Since the intensity of the laser light that ultimately enters the plasma processing chamber 86 is proportional to the intensity of the semiconductor laser 3000, the semiconductor laser 3000 may have a high output of several watts. Using a fiber bundle of multiple optical fibers, as shown in FIG. 4, is an effective method for guiding this high-output laser light. The laser light guided by the optical fiber 4000 is guided to the wavelength converter 5000 disposed in the laser illumination/scattered light detection optical system 2000.

The laser light entering the wavelength converter 5000 is focused by a focusing lens 5001 and illuminates a gain medium 5002 (e.g., a neodymium vanadate (Nd:VO4) crystal or a neodymium YAG (Nd:YAG) crystal). The gain medium 5002, e.g., neodymium vanadate, absorbs the excitation light with the 809 nm wavelength and discharges a powerful, uni-directional light at a wavelength of around 1064 nm. Neodymium vanadate, which is a material having different physical characteristics depending on the orientation of the crystal axis, also emits polarized laser light. The polarized light having a specific wavelength emitted by the gain medium 5002 is then converted to a different wavelength by a non-linear optical crystal 5004 (e.g., a crystal generating secondary harmonic frequencies) disposed in a resonator 5003. The non-linear optical crystal 5004, e.g., an LBO crystal, converts the laser light from a wavelength of 1064 nm to a wavelength of 532 nm. The resonator 5003 applies wavelength selection on the beam with the wavelength converted by the non-linear optical crystal 5004, forming a laser light 5008 with a narrow spectrum. Next, this polarized laser light 5008 with a narrow spectrum and a specific wavelength is converted to parallel light by a collimating lens 5005.

This parallel beam is converted to a P-polarized beam 101 by a half-wave plate 27 and enters an AO (Acousto-Optical) modulator 22. If the laser light 5008 is already P-polarized, the half-wave plate 27 is not needed. The AO modulator 22 receives a square-wave signal, e.g., with a frequency of 170 kHz preferably with a 50% duty cycle, from an oscillator 23 to provide intensity modulation of the P-polarized beam 101 at that frequency. In this embodiment, where the high-frequency voltage applied to the electrodes of the etching processing apparatus has a frequency of 400 kHz, the laser intensity modulation frequency should be a frequency such as 170 kHz that is different from 400 kHz and the harmonic frequencies thereof such as 800 kHz, 1.2 MHz, . . . . The reason for this will be described later.

The intensity-modulated P-polarized beam 102 [?101?] is focused at the center of the wafer W by a focusing lens 18, passes through a low-loss polarizing beam splitter 24, and is converted to a circularly polarized beam 103 by a quarter-wave plate 26. The beam is then reflected by a galvano-mirror 25 and is guided into the processing chamber through the observation window 10 disposed on a side surface of the plasma processing chamber 86. The galvano-mirror 25 is rotated so that the beam scans a plane roughly parallel to the wafer surface, thus providing illumination (particle detection) over the entire plane above the wafer.

The observation window 10 is reflected by the galvano-mirror 25 and passes through the quarter-wave plate 26 again to form S-polarized light, which is then reflected by the polarizing beam splitter 24 and enters a particle-scattered light detection optical fiber 3100, generating significant noise. To prevent noise from this light reflected off of the observation window, the observation window 10 is sloped so that light reflected from the surface is shifted from the detection optical axis, preventing detection.

Figure 5:
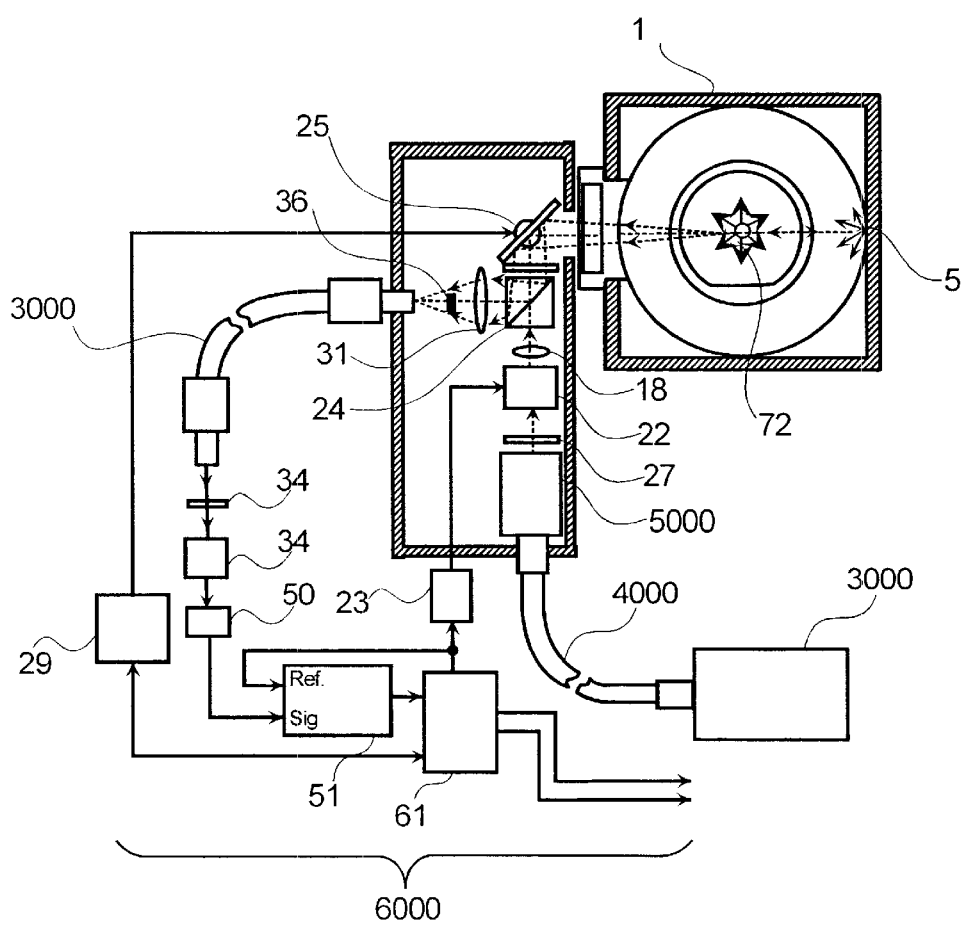
FIG. 5 is a drawing for the purpose of describing an optical system uses to detect light scattered by particles according to a first embodiment of the present invention.

Next, a method for detecting particle-scattered light will be described using FIG. 5 and FIG. 6. The circularly polarized beam 103 guided into the plasma processing chamber 86 is scattered by a suspended particle 72 in the plasma. Back-scattered light, which is the component of the particle-scattered light that propagates along the same optical axis as the circularly polarized beam 103, passes through the observation window 10, is reflected by the galvano-mirror 25, and extends to the polarizing beam splitter 24. The circularly polarized component of the back-scattered light, which corresponds to the directly reflected component, passes through the quarter-wave plate 26 again to form S-polarized light. This is reflected at a low loss by the polarizing beam splitter 24 and is focused on the entry plane of the particle-scattered light detection optical fiber 33 by a focusing lens 31.

As shown in FIG. 6, the wafer center 73b and the entry plane of the detection optical fiber 33 are in a focal relationship, but the light-receiving area of the entry end is large enough to allow detection of de-focused light scattered from the ends 73a, 73c of the wafer. As a result, particle-scattered light from the front of the wafer to the back can be detected at roughly the same sensitivity. To provide a large light-receiving plane, the method shown in FIG. 2 of using a fiber bundle is effective. The scattered light generated by an inner wall 5 of the processing chamber is focused in front of the light-receiving plane of the particle-scattered light detection optical fiber 33, so a spatial filter 36 is disposed at the focal position to block the light. The exit end of the particle-scattered light detection optical fiber 33 is connected to a spectroscope 34 formed from a monochrometer or interference filter set up for the wavelength of the polarized laser light 5008. This separates the wavelength component of the particle-scattered light from the plasma light. Then, opto-electric conversion is performed by an opto-electric converter 35.

The opto-electrically converted detection signal is amplified by an amp 50. A lock-in amp 51 performs synchronized detection using a signal output from the oscillator 23 used for intensity modulation of the laser light. The reference signal is a square-wave signal with a frequency of 170 kHz and a duty cycle of 50%. The particle-scattered light component having a frequency of 170 kHz is extracted from this detection signal.

Figure 7:
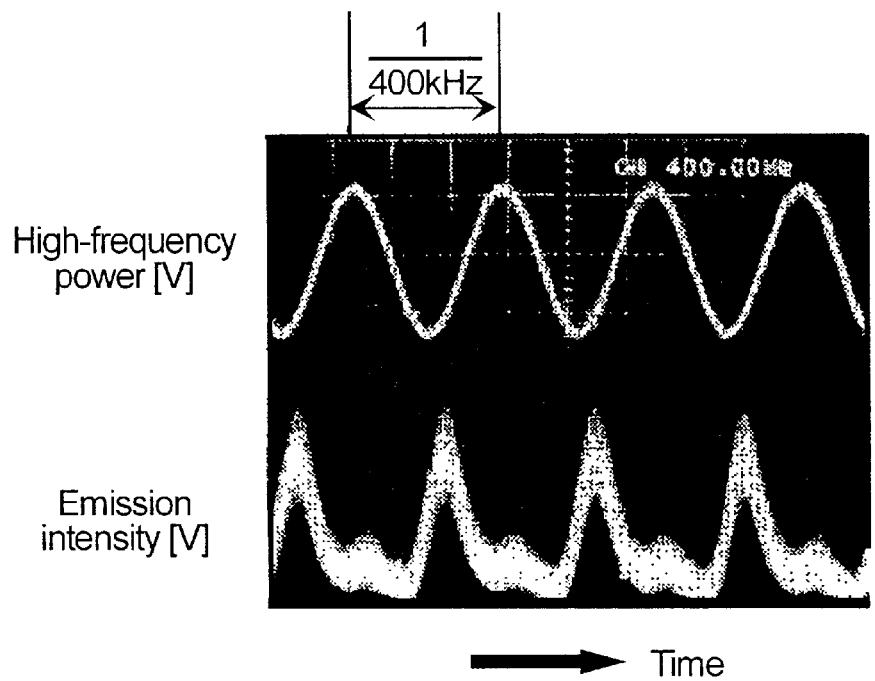
FIG. 7 is a drawing illustrating how the plasma excitation frequency and plasma emissions are synchronized in a first embodiment of the present invention.
Figure 7:
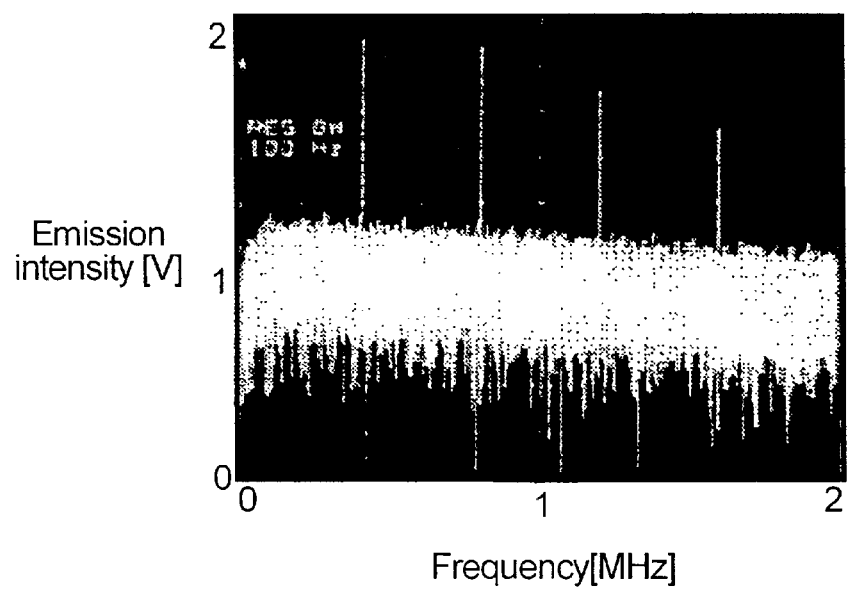
Figure 8:
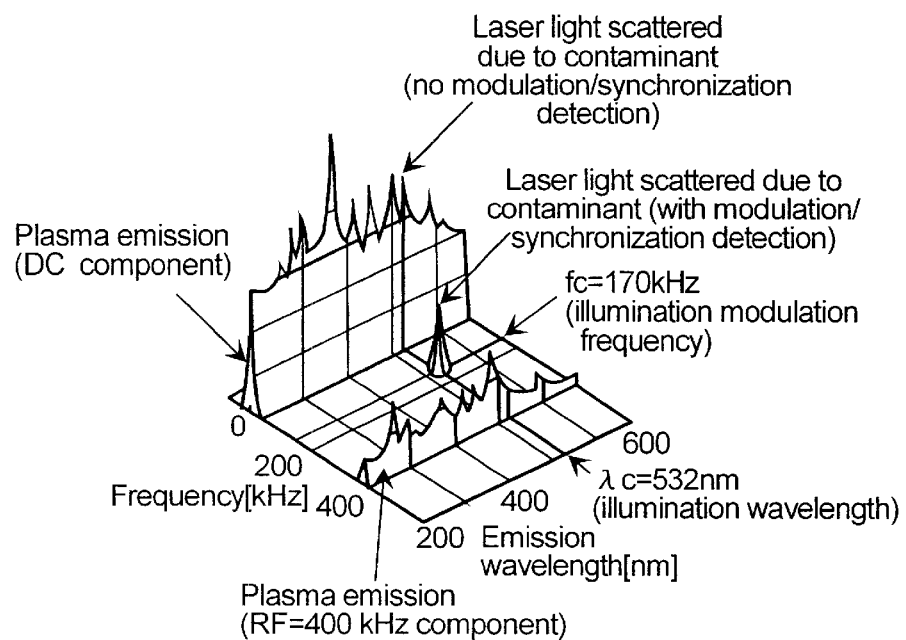
FIG. 8 is a drawing for the purpose of describing how wavelength/frequency separation of particle-scattered light from plasma emission takes place in the embodiments of the present invention.

As FIG. 7 shows, the inventors of the present invention have experimentally verified that the intensity of the plasma light is synchronized with the modulation frequency of the high-frequency voltage used for plasma excitation. For example, the light emitted from the plasma by the high-frequency voltage with a plasma excitation frequency of 400 kHz, as described above, is separated by wavelength using the spectroscope 34. Modulation and synchronized detection is performed at a frequency of 170 kHz, which is different from the plasma excitation frequency and integer multiples thereof. The resulting particle signal is separated from the plasma emission by wavelength and frequency, as shown in FIG. 8. The present inventors have experimentally confirmed that this method can be used to provide sensitive detection of very weak particle-scattered light in plasma emissions.

As shown in FIG. 8, the plasma emissions are distributed continuously over wavelength, but are arranged discretely over frequency, with empty regions. Thus, by projecting a laser light with a wavelength of, for example, 532 nm, that has been intensity modulated with a frequency different from the plasma emission frequency, e.g., 170 kHz, and extracting the 532 nm wavelength component and the 170 kHz component from the detected light, i.e., extracting only peak signals, the light scattered by particles can be separated from the plasma emissions and detected.

Figure 9:
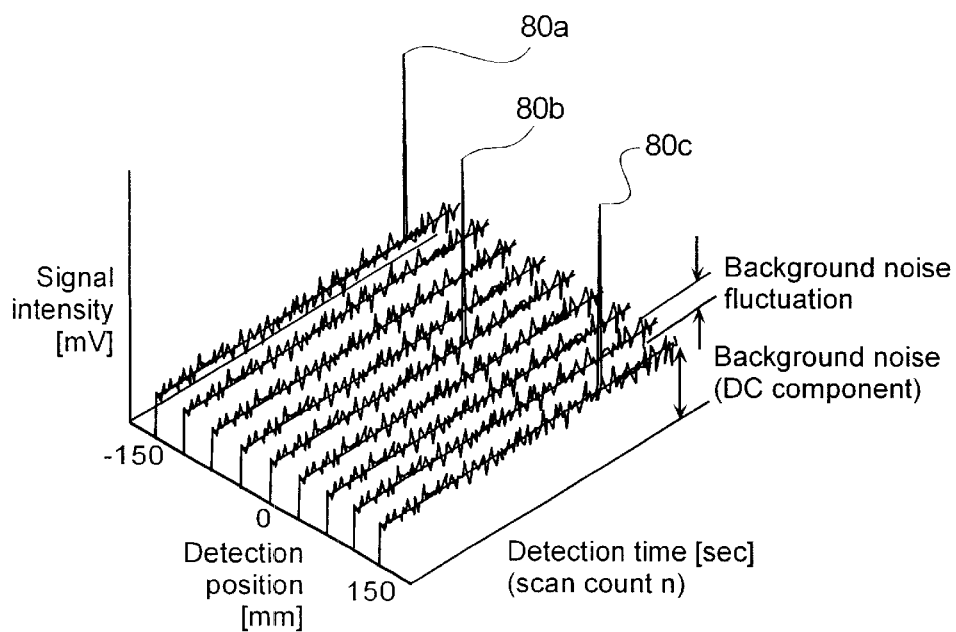
FIG. 9 is a drawing showing the variations over time of detected light intensity over nine points on the wafer according to a first embodiment of the present invention.

The output from the lock-in amp 51 is sent to the computer 61. The computer 61 sends a scan signal to the galvano-mirror 25 by way of the galvano driver 29, and a beam is scanned while the particle signal captured for the scanned positions are displayed sequentially on a display in a format such as shown in FIG. 9. This sample display shows signal intensities for scans by the illumination light 9 over a wafer with a diameter of 300 mm. When light is scattered by particles suspended in the plasma, large pulse signals such as the pulse signals 80a, 80b, 80c shown in FIG. 9 appear.

Figure 10:
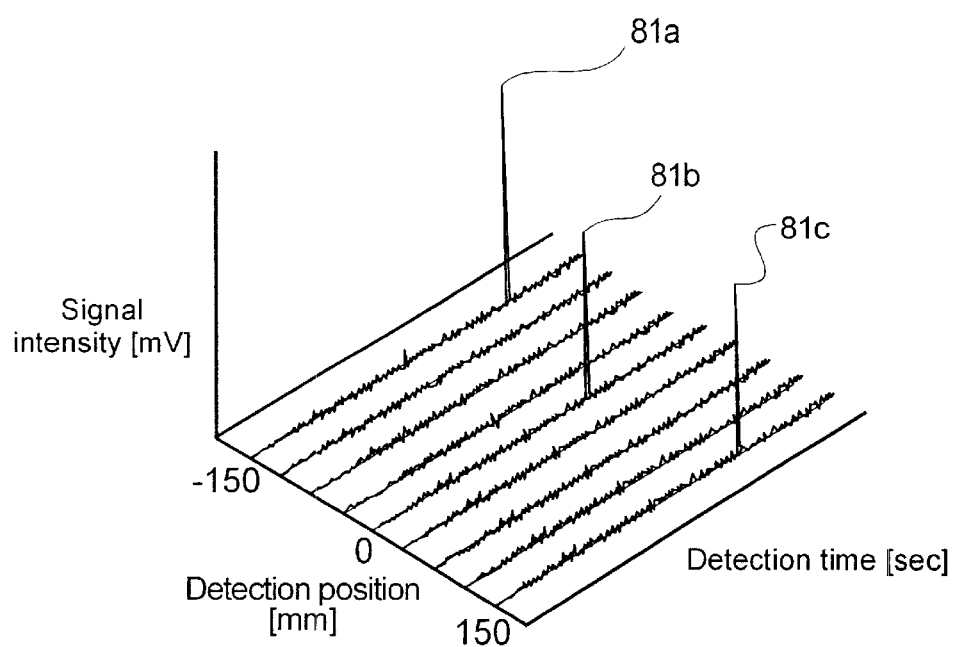
FIG. 10 is a drawing showing the variations over time of particle signal intensity over nine points on the wafer according to a first embodiment of the present invention.

As shown in FIG. 10, taking the difference between the output from the n-th scan and the output from the (n−1)-th scan cancels the DC component of background noise, allowing easy evaluation of particle signals. The computer 61 calculates particle sizes by comparing detected particle signal intensities with signal intensities associated with particle diameters as obtained from prior experiments. Also, the number of particles is determined from the pule signal. Also, particle positions are determined from the scan positions at which signals are detected. Furthermore, the computer 61 determines the contamination status inside the processing chamber based on the number and sizes of particles. If the total number of particles generated exceeds a reference value set up ahead of time, the etching operation can be halted and information can be output, e.g., an alarm or the like is used to notify a plasma processing apparatus operator.

In the embodiment described above, detection is performed for back-scattered light. This allows the laser illumination/scattered light detection optical systems to be formed as a single unit that can be used with processing apparatus that only have a single observation window 10. In addition, adjustment of optical axes and the like is easier compared to structures in which the illumination optical system and the detection optical system are formed separately, thus allowing the optical system as a whole to be more compact. The excitation light source, which is the element in the illumination light source that is the biggest heat source and that requires a large heat-dissipating heat sink, is separated from the laser illumination/scattered light detection optical system. As a result, the optical system as a whole can be made even more compact.

Also, compared to other elements in the plasma-suspended particle measuring apparatus, the excitation light source has a relatively short lifespan and can be expected to have a high frequency of being replaced. By separating this excitation light source from the laser illumination/scattered light detection optical system, the excitation light source can be replaced directly without having to manipulate the laser illumination/scattered light detection optical system. This improves maintenance efficiency and reduces the downtime of the apparatus.

Also, with the modulation/synchronized detection system used in this embodiment, weak particle-scattered light can be separated by wavelength and frequency from plasma emissions, which obstruct the detection of particles in plasma. Thus, compared to conventional methods that only separate by wavelength, the detection sensitivity for particles suspended in plasma can be improved significantly. With the conventional method using wavelength separation only, the minimum detection sensitivity was a diameter of about 1 micron. However, with the method of the present invention, the minimum detection sensitivity can be improved to a diameter of about 0.2 microns, thus allowing stable particle detection for the entire wafer surface. Also, since this embodiment uses detection of back-scattered light, the illumination beam can be rotationally scanned horizontally, thus allowing the two-dimensional distribution of particles to be easily known.

Also, this embodiment performs particle detection for the entire wafer surface and is able to determine the number, size, and distribution of particles. Thus, the operator can check this information in real time, e.g., through a display.

Since this embodiment allows real-time evaluation of the contamination status within the processing chamber based on the determined number, size, and distribution of particles, it would be possible, for example, to optimize the cleaning schedule and improve the operating efficiency of the apparatus. Also, clustered defects (large numbers of defects being generated all at once) can be prevented, leading to improved yield. Also, since processing proceeds while the contamination status in the processing chamber is continuously monitored, the semiconductor substrates and liquid crystal substrates produced in this manner will be produced in an environment that does not contain more than a predetermined level of particles, thus providing products with high quality and reliability.

Also, this embodiment can reduce the frequency of evaluations of processing chamber contamination using dummy wafers and contamination status evaluations via random inspections. Thus, the costs involved in the use of dummy wafers can be reduced.

Second Embodiment

Figure 11:
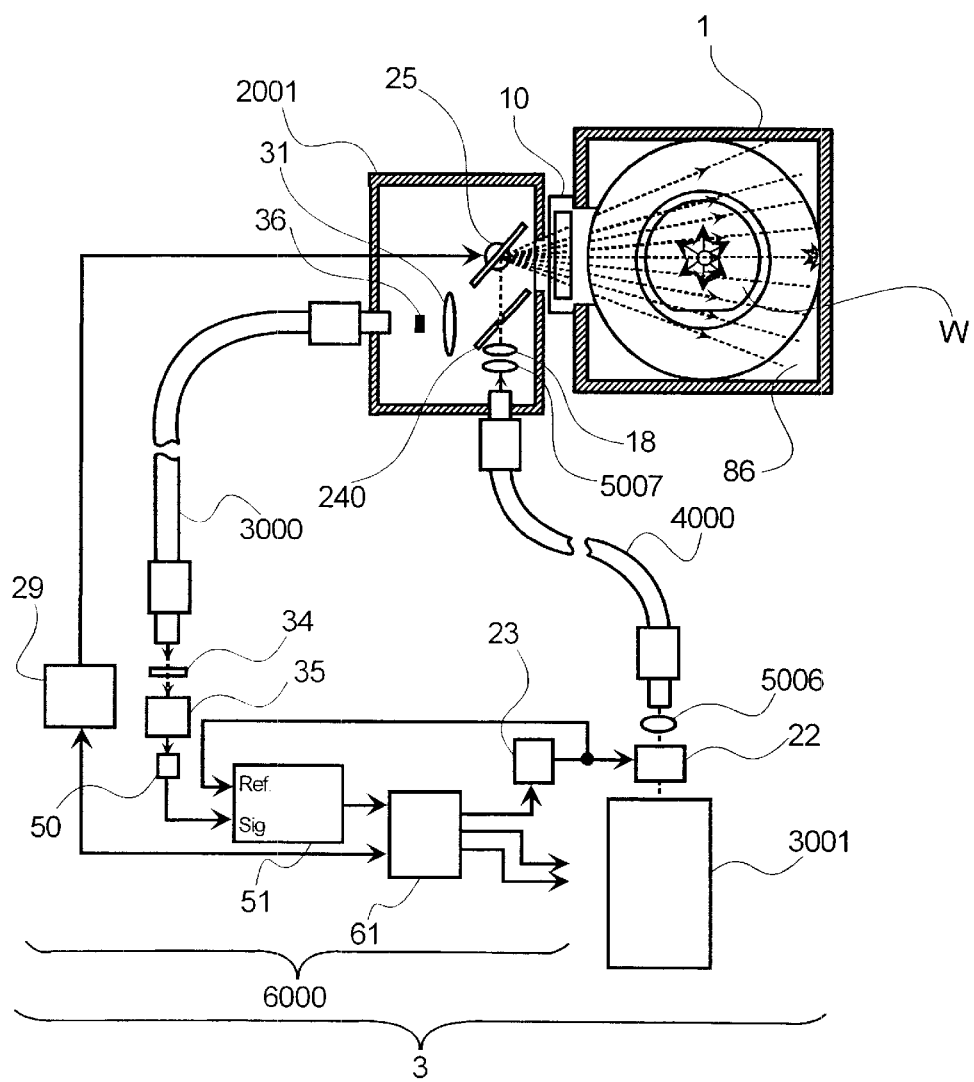
FIG. 11 is a drawing showing the architecture of an etching processing apparatus equipped with a apparatus for measuring particles suspended in plasma according to a second embodiment of the present invention
Figure 12:
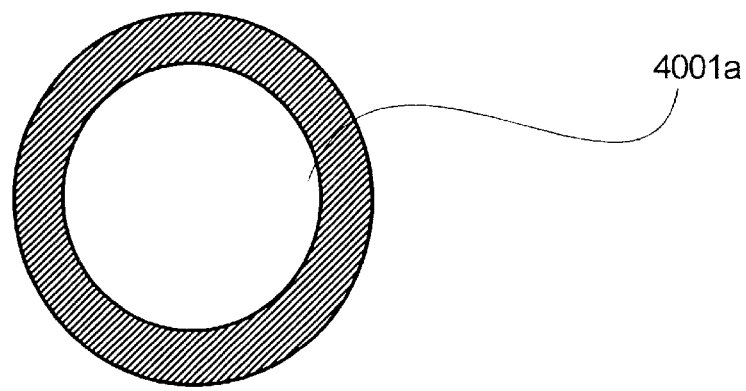
FIG. 12 is a cross-section drawing of a large-diameter fiber according to a second embodiment of the present invention.
Figure 13:
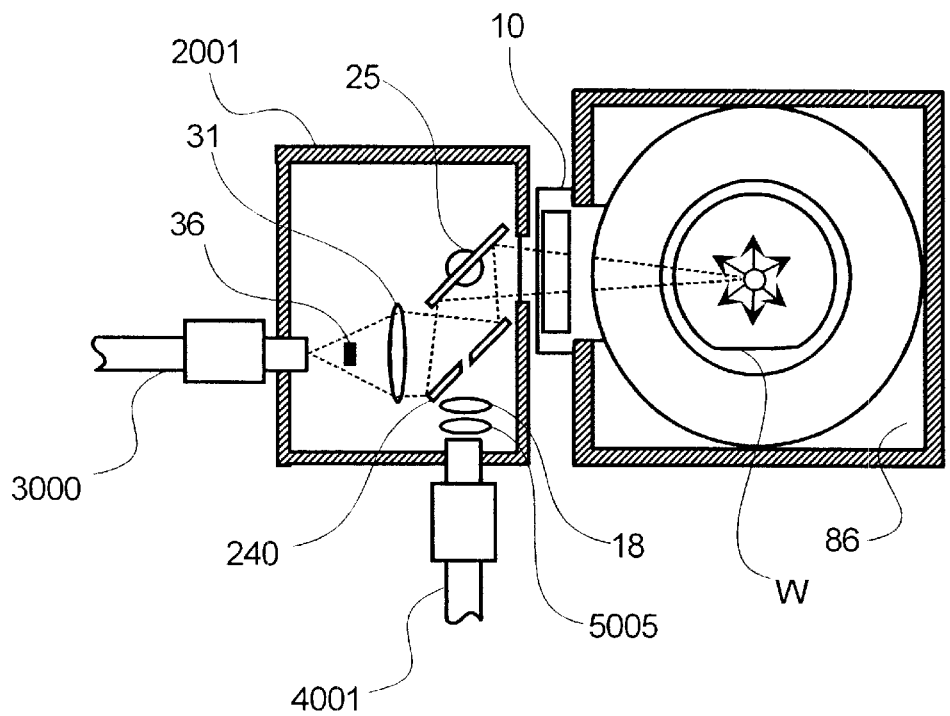
FIG. 13 is a drawing of an optical system for detecting particle-scattered light according to a second embodiment of the present invention.

Next, a plasma etching apparatus according to a second embodiment of the present invention will be described using FIG. 11 through FIG. 13. FIG. 11 is a drawing showing the architecture of an etching processing apparatus equipped with a plasma-suspended particle measuring apparatus according to the second embodiment.

In a etching processing apparatus 1 shown in FIG. 11, a high-frequency signal from the signal generator 83 modulates the output voltage from the power amp 84. This high-frequency voltage is distributed by the distributor 85 and applied to the upper electrode 81 and the lower electrode 82 oriented parallel to each other in the plasma processing chamber 86. Discharge between the electrodes generates the plasma 71 from the etching gas, resulting in the etching of the semiconductor substrate (wafer) W, which serves as the activation seed and the object of processing. The high-frequency signal can be, for example, a signal with a frequency of 400 kHz.

A plasma-suspended particle measuring apparatus 3 is formed primarily from a laser illumination/scattered light detection optical system 2001 and the control/signal processing system 6000. The illumination exit/detection light entry section of the laser illumination/scattered light detection optical system 2001 is positioned so that it faces the observation window 10 disposed on a side surface of the plasma processing chamber 86.

The difference between this and the first embodiment described above is that the illumination laser light source, which includes the excitation light source and the wavelength converter, is disposed outside of the laser illumination/scattered light detection optical system 2001. Thus, even if a high-output illumination is used so that the size of the laser light source increases (and the accompanying heat-dissipating heat sink increases in size), the laser illumination/scattered light detection optical system 2001 will not increase in size.

First, a laser beam from the laser light source 3001 (e.g., a solid-state laser with a wavelength of 532 nm and an output of about 500 mW) enters the AO modulator 22. The AO modulator 22 receives a square-wave signal, e.g., with a frequency of 170 kHz preferably with a 50% duty cycle, from the oscillator 23 to provide intensity modulation of the P-polarized beam 101 at that frequency. As with the first embodiment described above, in this embodiment, where the high-frequency voltage applied to the electrodes of the etching processing apparatus has a frequency of 400 kHz, the laser intensity modulation frequency should be a frequency such as 170 kHz that is different from 400 kHz and the harmonic frequencies thereof such as 800 kHz, 1.2 MHz, . . . . The intensity-modulated beam is guided to the laser illumination/scattered light detection optical system 2001 by a fiber bundle 4001. It would also be possible to use a large-diameter fiber as shown in FIG. 12 in place of the fiber bundle 4001. This type of large-diameter fiber has the advantage of a large core diameter and allows beams to enter relatively easily with low loss.

The beam existing from the fiber bundle or the large-diameter fiber is an unpolarized beam. The laser light entering the laser illumination/scattered light detection optical system 2001 is focused at the center of the wafer W by the focusing lens 18. The focused beam passes through a hole larger enough for the beam formed on a mirror 240. The beam is reflected by the galvano-mirror 25 and is guided into the processing chamber through the observation window 10 disposed on a side surface of the plasma processing chamber 86. The galvano-mirror 25 is rotated to scan the beam along a plane roughly parallel to the wafer surface, thus providing illumination (particle detection) over the entire plane over the wafer.

Light reflected from the observation window 10 is reflected by the galvano-mirror 25 and is then reflected by the mirror 240 and enters a particle-scattered light detection optical fiber 3100. As in the first embodiment described above, the observation window 10 is sloped to prevent noise.

Next, a method for detecting particle-scattered light will be described using FIG. 13. The unpolarized illumination beam guided into the plasma processing chamber 86 is scattered by a suspended particle 72 in the plasma. Back-scattered light, which is the component of the particle-scattered light that propagates along the same optical axis as the unpolarized illumination beam, passes through the observation window 10 and is reflected by the galvano-mirror 25 and the mirror 240. The light is then focused on the entry plane of the particle-scattered light detection optical fiber 33 by the focusing lens 31. As with the first embodiment described above, the wafer center 73b and the entry plane of the particle-scattered light detection optical fiber 33 are in a focal relationship as shown in FIG. 6, but the light-receiving area of the entry end is large enough to allow detection of de-focused light scattered from the ends 73a, 73c of the wafer. As a result, particle-scattered light from the front of the wafer to the back can be detected at roughly the same sensitivity. The scattered light generated by an inner wall 5 of the processing chamber is focused in front of the light-receiving plane of the particle-scattered light detection optical fiber 33, so a spatial filter 36 is disposed at the focal position to block the light. The subsequent apparatus architecture and functions provided for signal processing and evaluating contamination generation are similar to the first embodiment described above, so their descriptions will be omitted.

With this embodiment as described above, detection is performed for back-scattered light. This allows the laser illumination/scattered light detection optical systems to be formed as a single unit that can be used with processing apparatus that only have a single observation window 10. In addition, adjustment of optical axes and the like is easier compared to structures in which the illumination optical system and the detection optical system are formed separately, thus allowing the optical system as a whole to be more compact. Furthermore, by separating the large excitation light source from the laser illumination/scattered light detection optical systems, the optical system as a whole can be made more compact.

Also, compared to other elements in the plasma-suspended particle measuring apparatus, the excitation light source has a relatively short lifespan and can be expected to have a high frequency of being replaced. By separating this excitation light source from the laser illumination/scattered light detection optical system, the excitation light source can be replaced directly without having to manipulate the laser illumination/scattered light detection optical system. This improves maintenance efficiency and reduces the downtime of the apparatus.

Also, with the modulation/synchronized detection system used in this embodiment, weak particle-scattered light can be separated by wavelength and frequency from plasma emissions, which obstruct the detection of particles in plasma. Thus, compared to conventional methods that only separate by wavelength, the detection sensitivity for particles suspended in plasma can be improved significantly. With the conventional method using wavelength separation only, the minimum detection sensitivity was a diameter of about 1 micron. However, with the method of the present invention, the minimum detection sensitivity can be improved to a diameter of about 0.2 microns, thus allowing stable particle detection for the entire wafer surface.

Also, since this embodiment uses detection of back-scattered light, the illumination beam can be rotationally scanned horizontally, thus allowing the two-dimensional distribution of particles to be easily known.

Also, this embodiment performs particle detection for the entire wafer surface and is able to determine the number, size, and distribution of particles. Thus, the operator can check this information in real time, e.g., through a display.

Since this embodiment allows real-time evaluation of the contamination status within the processing chamber based on the determined number, size, and distribution of particles, it would be possible, for example, to optimize the cleaning schedule and improve the operating efficiency of the apparatus. Also, clustered defects (large numbers of defects being generated all at once) can be prevented, leading to improved yield. Also, since processing proceeds while the contamination status in the processing chamber is continuously monitored, the semiconductor substrates and liquid crystal substrates produced in this manner will be produced in an environment that does not contain more than a predetermined level of particles, thus providing products with high quality and reliability.

Also, this embodiment can reduce the frequency of evaluations of processing chamber contamination using dummy wafers and contamination status evaluations via random inspections. Thus, the costs involved in the use of dummy wafers can be reduced.

Third Embodiment

Figure 14:
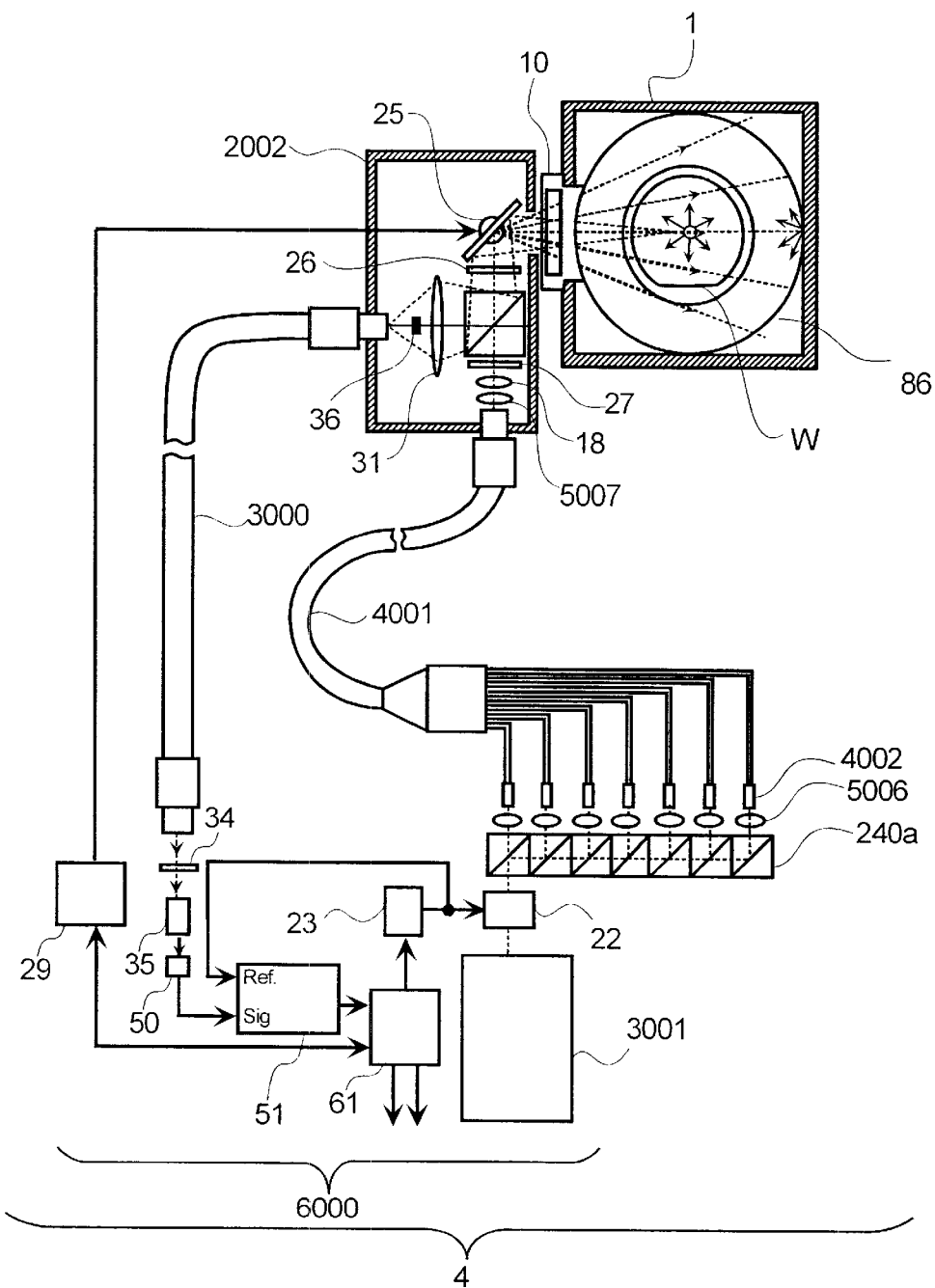
FIG. 14 is a drawing of an etching apparatus equipped with a apparatus for measuring particles suspended in plasma according to a third embodiment of the present invention.

Next, a plasma etching apparatus according to a third embodiment of the present invention will be described using FIG. 14 through FIG. 17. FIG. 14 shows the architecture of an etching processing apparatus equipped with a plasma-suspended particle measuring apparatus according to the third embodiment.

As shown in FIG. 14, the etching processing apparatus uses a high-frequency signal from the signal generator 83 to modulate the output voltage from the power amp 84. This high-frequency voltage is distributed by the distributor 85 and applied to the upper electrode 81 and the lower electrode 82 oriented parallel to each other in the plasma processing chamber 86. The discharge between these electrodes generates the plasma 71 from the etching gas, resulting in the etching of the semiconductor substrate (wafer) W, which serves as the activation seed and the object of processing. The high-frequency signal can be, for example, a signal with a frequency of 400 kHz.

The plasma-suspended particle measuring apparatus 4 is formed primarily from a laser illumination/scattered light detection optical system 2002, the laser light source 3001, a beam splitter 240a, a polarization plane retention fiber 4002, a polarization plane retention fiber bundle 4001, and the control/signal processing system 6000. The illumination exit/detection light entry section of the laser illumination/scattered light detection optical system 2002 is positioned so that it faces the observation window 10 disposed on a side surface of the plasma processing chamber 86.

The difference between this embodiment and the first embodiment and the second embodiment described above is that the laser beam from the illumination laser light source is split into multiple beams, and each of the split beams are coupled to a polarization plane retention fiber. These polarization plane retention fibers are bundled so that their polarization directions are all the same at the exit plane. The polarized laser light from these bundled polarization plane retention fibers are guided to the laser illumination/scattered light detection optical system 2002. Thus, high-power polarized laser illumination can be provided without increasing the size of the laser illumination/scattered light detection optical system 2002.

First, a laser beam from the laser light source 3001 (e.g., a solid-state laser with a wavelength of 532 nm and an output of about 500 mW) enters the AO modulator 22. The AO modulator 22 receives a square-wave signal, e.g., with a frequency of 170 kHz preferably with a 50% duty cycle, from the oscillator 23 to provide intensity modulation of the P-polarized beam 101 at that frequency. As with the first and second embodiment described above, in this embodiment, where the high-frequency voltage applied to the electrodes of the etching processing apparatus has a frequency of 400 kHz, the laser intensity modulation frequency should be a frequency such as 170 kHz that is different from 400 kHz and the harmonic frequencies thereof such as 800 kHz, 1.2 MHz, . . . .

Figure 15:
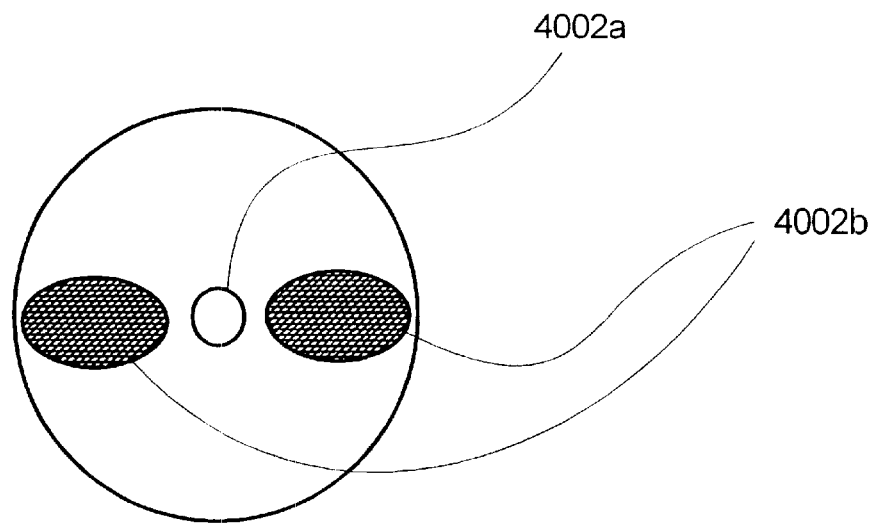
FIG. 15 is a cross-section drawing of a polarization plane retention fiber according to a third embodiment of the present invention.

The intensity-modulated laser light is split seven ways by the beam splitter. In this embodiment, the number of split beams is seven, but the number of split beams is not restricted to seven and can be any number. Each of these split beams is coupled to a polarization plane retention fiber 4002 using a coupling lens. As shown in FIG. 15, the polarization plane retention fibers are formed with stress-applying sections 4002b around a core 4002a. The core 4002a is smaller than those of standard optical fibers (e.g., a few microns for a laser wavelength of 532 nm). A high-power laser beam can result in damage to the entry plane so that the beam is reflected rather than entering the fiber. To prevent this, this embodiment splits the beam and reduces the strength of the split beams to allow them to enter the polarization plane retention fibers.

Figure 16:
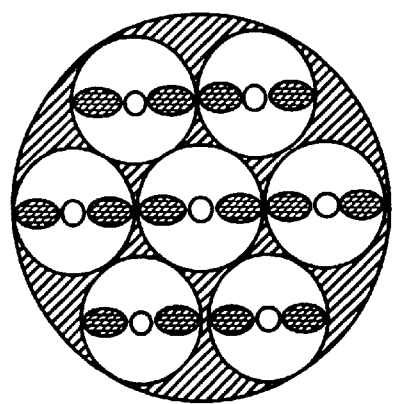
FIG. 16 is a cross-section drawing of a polarization plane retention fiber bundle according to a third embodiment of the present invention.
Figure 17:
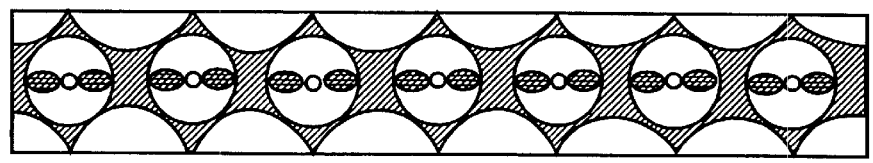
FIG. 17 is a cross-section drawing of a polarization plane retention fiber bundle according to a third embodiment of the present invention.

Next, the polarization plane retention fibers are arranged in an array so that the polarization directions of all the exit planes are oriented in the same direction as shown, for example, in FIG. 16 and FIG. 17. The polarization plane retention fiber bundle 4001 then guides the light to the laser illumination/scattered light detection optical system 2002. The laser light entering the laser illumination/scattered light detection optical system 2002 is converted to parallel light by a collimating lens 5005 and is then focused at the center of the wafer W. Next, after the focused laser light is converted to P-polarized light by the half-wave plate 27, it is passed through the polarizing beam splitter 24 at a low loss. The quarter-wave plate 26 then converts this light to a circularly polarized beam 103, which is reflected by the galvano-mirror 25 and guided into the processing chamber through the observation window 10 disposed on a side surface of the plasma processing chamber 86. The galvano-mirror 25 is rotated so that the beam scans a plane roughly parallel to the wafer surface, thus allowing illumination (particle detection) over the entire surface of the wafer. If the beam exiting from the polarization plane retention fiber bundle 4001 is already P-polarized, there is no need for the half-wave plate 27.

The subsequent apparatus architecture and functions provided for signal processing and evaluating contamination generation are similar to the first embodiment described above, so their descriptions will be omitted.

In the embodiment described above, detection is performed for back-scattered light. This allows the laser illumination/scattered light detection optical systems to be formed as a single unit that can be used with processing apparatus that only have a single observation window 10. In addition, adjustment of optical axes and the like is easier compared to structures in which the illumination optical system and the detection optical system are formed separately, thus allowing the optical system as a whole to be more compact. The excitation light source, which is the element in the illumination light source that is the biggest heat source and that requires a large heat-dissipating heat sink, is separated from the laser illumination/scattered light detection optical system. As a result, the optical system as a whole can be made even more compact.

Also, compared to other elements in the plasma-suspended particle measuring apparatus, the excitation light source has a relatively short lifespan and can be expected to have a high frequency of being replaced. By separating this excitation light source from the laser illumination/scattered light detection optical system, the excitation light source can be replaced directly without having to manipulate the laser illumination/scattered light detection optical system. This improves maintenance efficiency and reduces the downtime of the apparatus.

Also, this embodiment allows a high-power polarized laser beam to be guided to the laser illumination/scattered light detection optical system from outside.

Also, with the modulation/synchronized detection system used in this embodiment, weak particle-scattered light can be separated by wavelength and frequency from plasma emissions, which obstruct the detection of particles in plasma. Thus, compared to conventional methods that only separate by wavelength, the detection sensitivity for particles suspended in plasma can be improved significantly. With the conventional method using wavelength separation only, the minimum detection sensitivity was a diameter of about 1 micron. However, with the method of the present invention, the minimum detection sensitivity can be improved to a diameter of about 0.2 microns, thus allowing stable particle detection for the entire wafer surface.

Also, since this embodiment uses detection of back-scattered light, the illumination beam can be rotationally scanned horizontally, thus allowing the two-dimensional distribution of particles to be easily known.

Also, this embodiment performs particle detection for the entire wafer surface and is able to determine the number, size, and distribution of particles. Thus, the operator can check this information in real time, e.g., through a display.

Since this embodiment allows real-time evaluation of the contamination status within the processing chamber based on the determined number, size, and distribution of particles, it would be possible, for example, to optimize the cleaning schedule and improve the operating efficiency of the apparatus. Also, clustered defects (large numbers of defects being generated all at once) can be prevented, leading to improved yield. Also, since processing proceeds while the contamination status in the processing chamber is continuously monitored, the semiconductor substrates and liquid crystal substrates produced in this manner will be produced in an environment that does not contain more than a predetermined level of particles, thus providing products with high quality and reliability.

Also, this embodiment can reduce the frequency of evaluations of processing chamber contamination using dummy wafers and contamination status evaluations via random inspections. Thus, the costs involved in the use of dummy wafers can be reduced.

Fourth Embodiment

Figure 18:
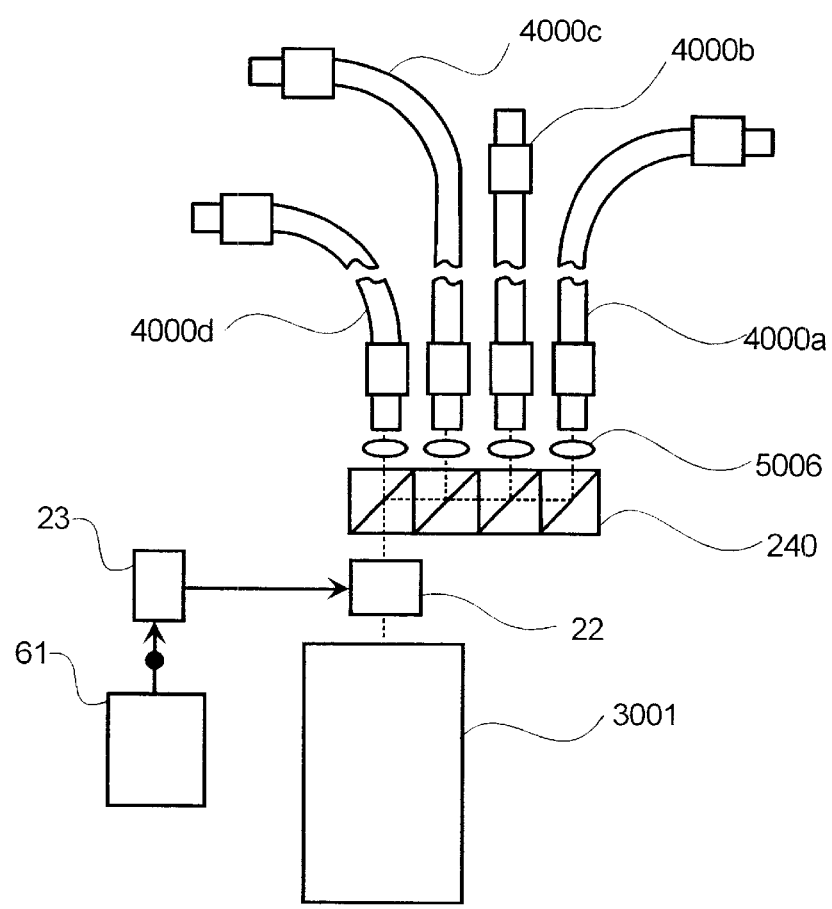
FIG. 18 is a drawing showing an external laser light source according to a fourth embodiment of the present invention.

The following is a description of a light source system supplying a laser light source to a laser illumination/scattered light detection optical system in a plasma-suspended particle measuring apparatus according to a fourth embodiment of the present invention, with references to FIG. 18. In this embodiment, the laser beam is split into multiple beams, which are coupled to multiple fiber bundles or to a large-diameter fiber, with the output from the fiber bundles or large-diameter fiber being guided to the laser illumination/scattered light detection optical system 2001 from the second embodiment described above. Since the architecture and functions of the etching processing apparatus equipped with a plasma-suspended particle measuring apparatus are similar to those of the second embodiment described above, corresponding figures and descriptions will be omitted.

First, a laser beam from the laser light source 3001 (e.g., a solid-state laser with a wavelength of 532 nm and an output of about 500 mW) enters the AO modulator 22. The AO modulator 22 receives a square-wave signal, e.g., with a frequency of 170 kHz preferably with a 50% duty cycle, from the oscillator 23 to provide intensity modulation of the P-polarized beam 101 at that frequency. In this embodiment, where the high-frequency voltage applied to the electrodes of the etching processing apparatus has a frequency of 400 kHz, the laser intensity modulation frequency should be a frequency such as 170 kHz that is different from 400 kHz and the harmonic frequencies thereof such as 800 kHz, 1.2 MHz, . . . . The reason for this is as described in the first embodiment.

The intensity-modulated beam is split four ways by a beam splitter. In this embodiment, the number of split beams is four, but the number of split beams is not restricted to four and can be any number. These split beams are coupled to a fiber bundle 4000a through a fiber bundle 4000d using coupling lenses 5006. These bundled fibers 4000a through 4000d are guided to the laser illumination/scattered light detection optical system 2001 from the second embodiment described above.

The subsequent apparatus architecture and functions provided for signal processing and evaluating contamination generation are similar to the second embodiment described above, so their descriptions and figures will be omitted.

In addition to the advantages provided by the second embodiment described above, this embodiment allows a single laser light source to be used for multiple etching processing apparatus equipped with plasma-suspended particle measuring apparatus. This reduces costs.

Fifth Embodiment

Figure 19:
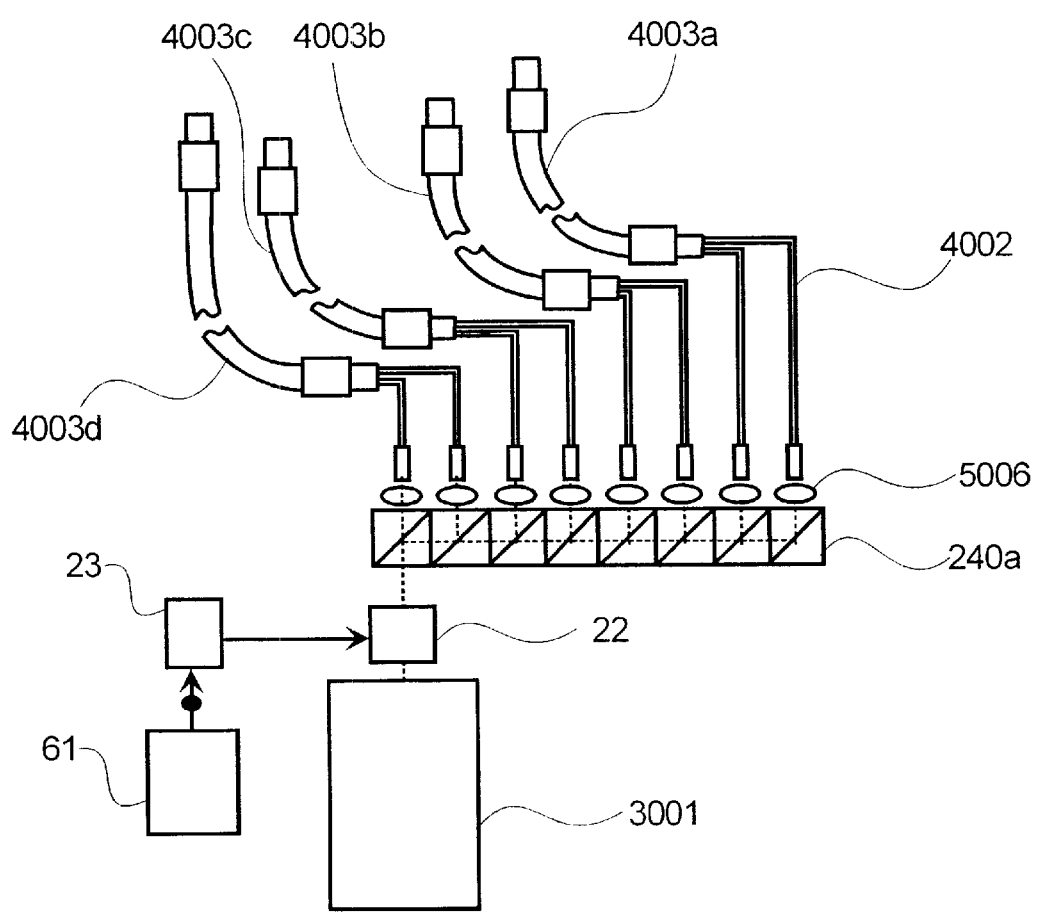
FIG. 19 is a drawing showing an external laser light source according to a fifth embodiment of the present invention.

Next, a plasma etching apparatus according to a fifth embodiment of the present invention will be described using FIG. 19. In this embodiment, a laser beam is split into multiple beams, with each beam being coupled to a polarization plane retention fiber. These polarization plane retention fibers are grouped in several sets and bundled so that the polarization directions match at the exit planes. Each of the polarization plane retention fiber bundles are guided to the laser illumination/scattered light detection optical system 2003 from the third embodiment described above. Since the architecture and functions of the etching processing apparatus equipped with a plasma-suspended particle measuring apparatus are similar to those of the third embodiment described above, corresponding figures and descriptions will be omitted.

A laser beam from the laser light source 3001 (e.g., a solid-state laser with a wavelength of 532 nm and an output of about 500 mW) enters the AO modulator 22. The AO modulator 22 receives a square-wave signal, e.g., with a frequency of 170 kHz preferably with a 50% duty cycle, from the oscillator 23 to provide intensity modulation of the P-polarized beam 101 at that frequency. In this embodiment, where the high-frequency voltage applied to the electrodes of the etching processing apparatus has a frequency of 400 kHz, the laser intensity modulation frequency should be a frequency such as 170 kHz that is different from 400 kHz and the harmonic frequencies thereof such as 800 kHz, 1.2 MHz, . . . . The reason for this is as described in the first embodiment.

The intensity-modulated laser light is split eight ways by a beam splitter. In this embodiment, the number of split beams is eight, but the number of split beams is not restricted to eight and can be any number. These split beams are coupled to a polarization plane retention fiber 4002a through a polarization plane retention fiber 4002d using the coupling lenses 5006. Pairs of these fibers are bundled to form four sets of polarization plane retention fiber bundles. In this embodiment, eight polarization plane retention fibers are bundled to form four polarization plane retention fiber bundles, but the number of bundles is not restricted to this. Various combinations can be used. For example, the fibers can be individually guided to the plasma-suspended particle measuring apparatus or the fibers can be divided into two polarization plane retention fiber bundles. Next, the polarization plane retention fiber bundles 4002a through 4002d are guided to the laser illumination/scattered light detection optical system 2002 from the third embodiment described above. The subsequent apparatus architecture and functions provided for signal processing and evaluating contamination generation are similar to the third embodiment described above, so their descriptions and figures will be omitted.

In addition to the advantages of the third embodiment described above, this embodiment allows a single laser light source to be used for multiple etching processing apparatus equipped with plasma-suspended particle measuring apparatus. This reduces costs.

Sixth Embodiment

Figure 20:
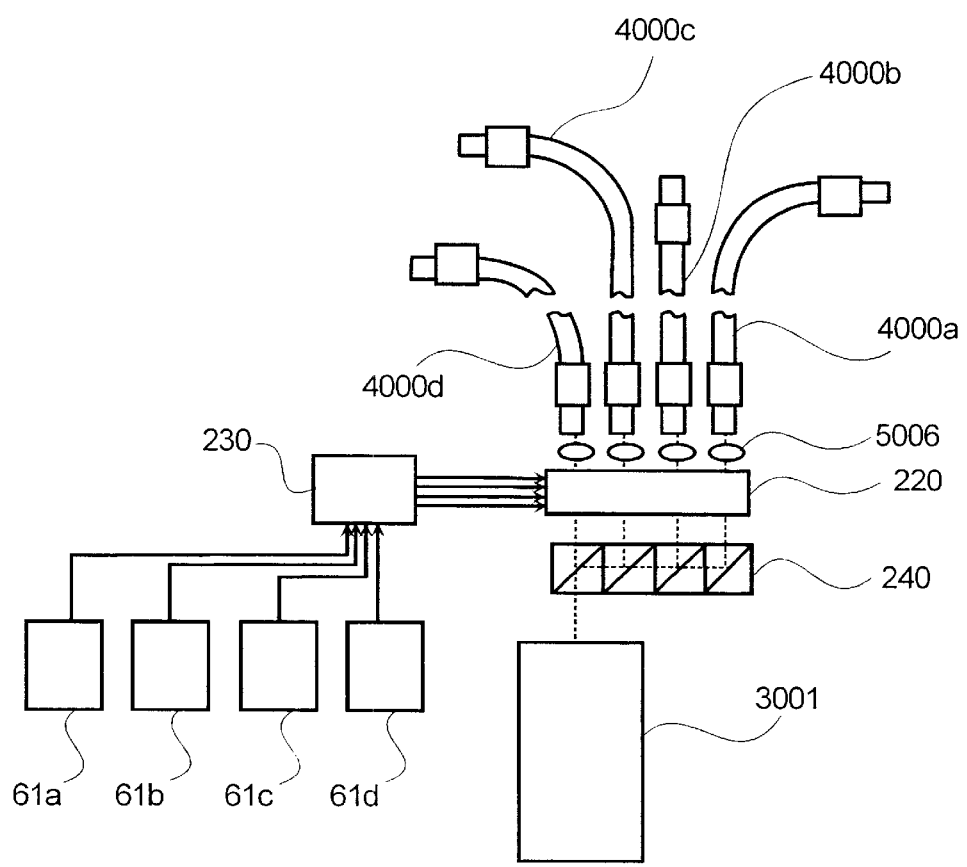
FIG. 20 is a drawing showing an external laser light source according to a sixth embodiment of the present invention.

Next, a plasma etching apparatus according to a sixth embodiment of the present invention will be described using FIG. 20. In this embodiment, a laser light is split into multiple beams, each of which is intensity modulated by an AO modulator and coupled with a fiber bundle or large-diameter fiber. The output from the fiber bundles or large-diameter fibers is guided to the laser illumination/scattered light detection optical system 2001 from the second embodiment described above. The subsequent apparatus architecture and functions provided for signal processing and evaluating contamination generation are similar to the second embodiment described above, so their descriptions and figures will be omitted.

A laser beam from the laser light source 3001 (e.g., a solid-state laser with a wavelength of 532 nm and an output of about 500 mW) is split four ways by a beam splitter. In this embodiment, the number of split beams is four, but the number of split beams is not restricted to four and can be any number. The split beams are sent to a multi-channel AO modulator 220.

The AO modulator 220 receives square-wave signals with frequencies output from a computer 61a through a computer 61d and preferably a duty cycle of 50%. Intensity modulation is performed with these frequencies. These frequencies are set appropriately, taking into account the frequency of the high-frequency voltage applied to the electrodes of the etching processing apparatus. The intensity-modulated beams are coupled to a fiber bundle 4000a through a fiber bundle 4000d by the coupling lenses 5006. Then, the fiber bundles 4000a through 4000d are guided to the laser illumination/scattered light detection optical system 2001 from the second embodiment described above. The subsequent apparatus architecture and functions provided for signal processing and evaluating contamination generation are similar to those of the second embodiment described above, so their descriptions will be omitted.

In addition to the advantages provided by the second embodiment and the fifth embodiment, this embodiment as described above allows a multi-functional etching processing apparatus equipped with a plasma-suspended particle measuring apparatus that can use different plasma excitation frequencies.

Seventh Embodiment

Figure 21:
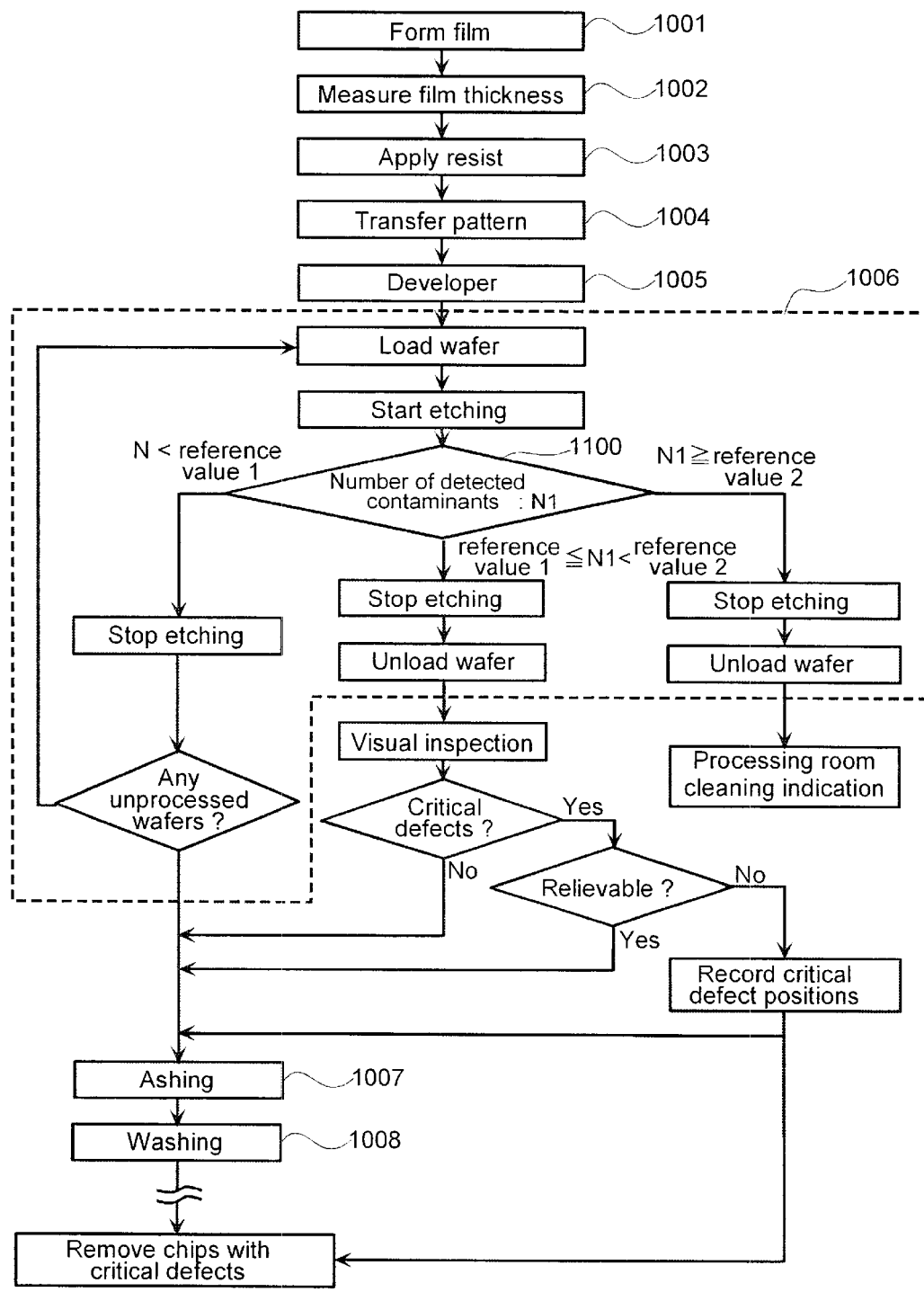
FIG. 21 is a drawing schematically illustrating the production processes of a semiconductor integrated circuit apparatus in which is used an etching processing apparatus equipped with a apparatus for measuring particles suspended in plasma according to a seventh embodiment of the present invention.
Figure 22:
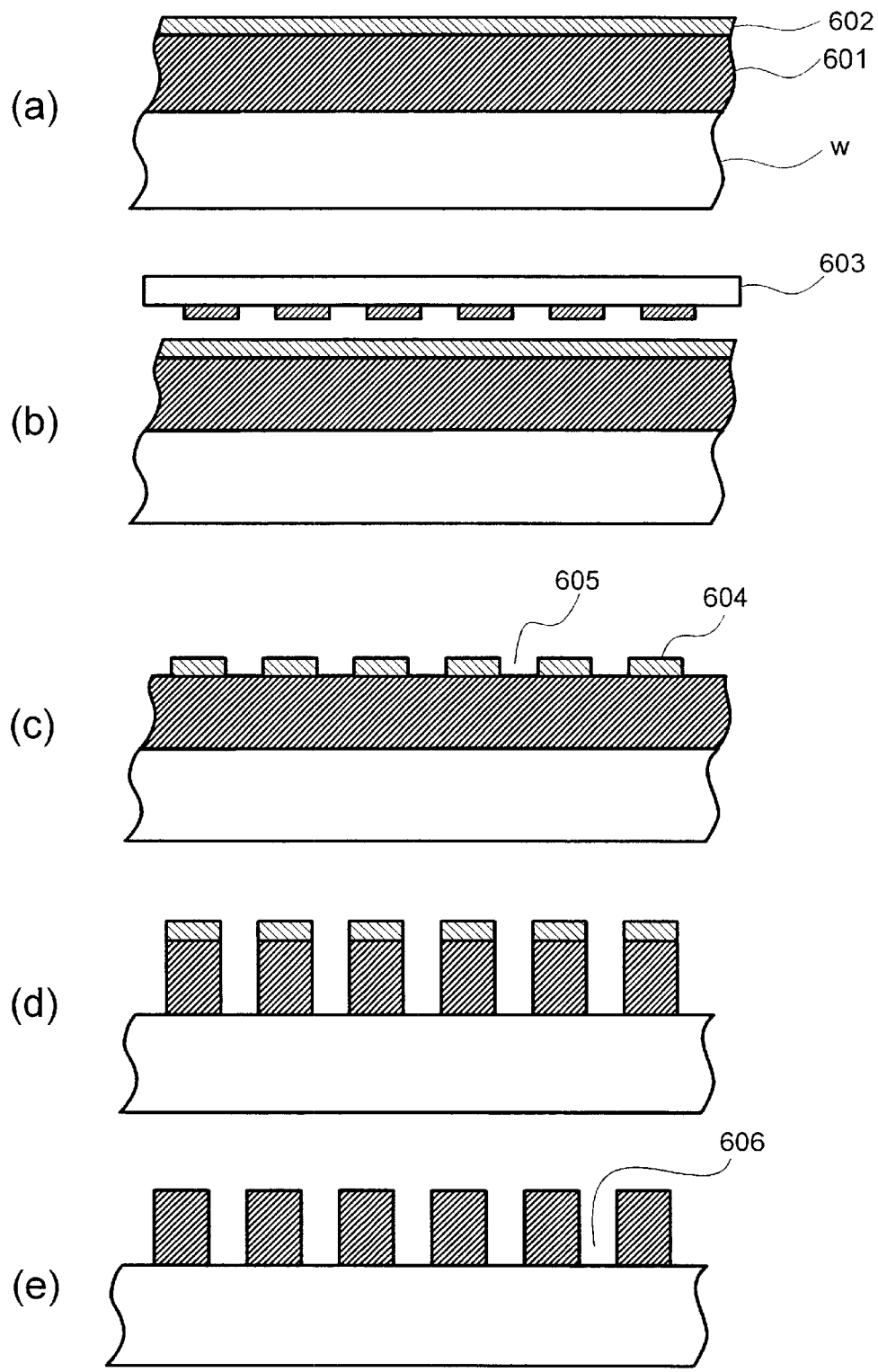
FIGS. 22A–E is a schematic drawing for the purpose of describing with cross-section structures the flow of operations in a contact hole forming process according to a seventh embodiment of the present invention.
Figure 23:
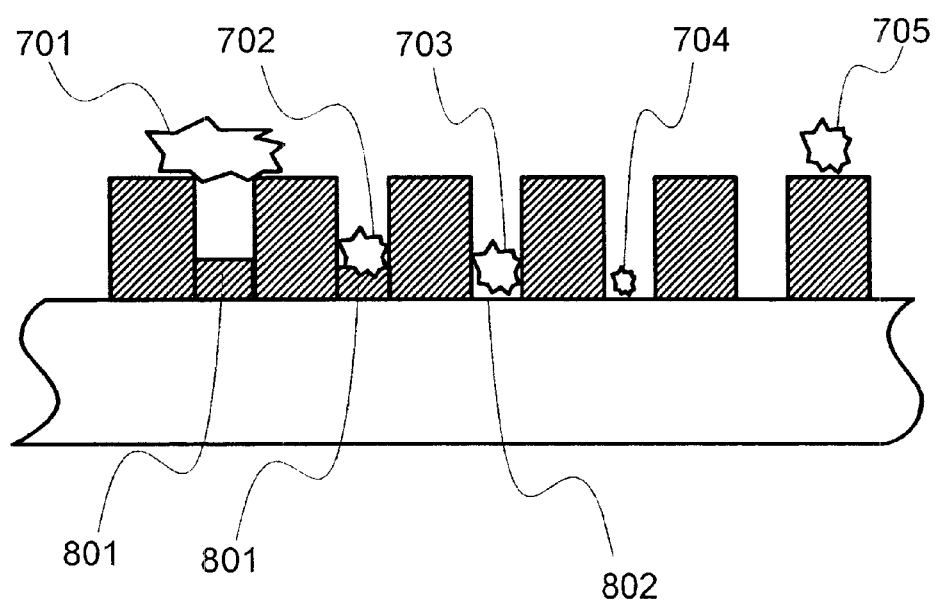
FIG. 23 is a cross-section drawing of a substrate to be processed that schematically shows a defect generated by an adhered particle in a contact hole etching process according to a seventh embodiment of the present invention.

Next, an eighth embodiment of the present invention will be described using FIG. 21, FIG. 22, and FIG. 23.

First, an overview of a method for producing semiconductor integrated circuit apparatus according to the present invention will be described using FIG. 19, FIG. 20, and FIG. 21.

Step 1001 is a film forming step in which a film 601 such as a silicon oxide film is formed on the wafer W. Step 1002 is a film thickness measuring step for inspecting the thickness of the film that was formed. Step 1003 is a resist applying step, in which a resist 602 is applied to the wafer W. Step 1004 is a pattern transfer step for transferring a mask pattern 603 to the wafer. Step 1005 is a developing step that eliminates the resist over the sections to be processed. Step 1006 is an etching step, where resist removal sections 605 of the film 601 is etched using the resist pattern 604 as a mask, thus forming circuit grooves and contact holes 606. Step 1007 is an ashing step that removes the resist pattern 604. Step 1008 is a cleaning step for cleaning the surface and back surface of the wafer. This series of steps is used, for example, to form contact holes.

In standard semiconductor integrated circuit apparatus, this series of steps is repeated to form a multi-layer structure.

Next, using FIG. 23, defects created by the adhesion to the wafer of particles generated during etching will be described. FIG. 23 shows an example in which defects are generated when contact holes are etched.

A particle 701 indicates a particle adhered to a contact hole opening during the etching operation. In this case, the adhered particle stops the etching reaction. This closes off the contact hole where the particle is attached, resulting in a killer defect.

A particle 702 indicates a particle adhered inside a contact hole during the etching operation. The etching reaction is stopped in this case as well due to the adhesion of the particle. This closes off the contact hole where the particle is attached, resulting in a killer defect.

A particle 703 and a particle 704 indicate particles adhered inside contact holes after the etching operation is finished. In places such as contact holes that have high aspect ratios, particles can often be difficult to remove through cleaning. If the particle is large, as in the particle 703, a bad contact may result, causing a killer defect.

A particle 705 indicates a particle adhered to the resist pattern 604 during etching. In this case, the adhered particle 705 does not affect the etching reaction at all. Thus, the adhered particle 705 will not lead to a killer defect.

In this manner, the adhesion of a particle will not lead to a killer defect if the size of the particle is not large enough to lead to a defect or if the position of the particle is a non-etching region. Thus, even if particles are adhered to the wafer, not all of them will lead to killer defects. Also, while the particle 701 and the particle 705 are particles that can be easily cleaned off, removal through cleaning is difficult for particles that have dropped into a contact hole having a high aspect ratio, e.g., the particle 602, the particle 703, and the particle 704.

In the present invention, a plasma-suspended particle measuring apparatus 1100 is used at the etching step 1006 to detect in real time the particles generated in the processing chamber during etching. Based on these particle detection results, a decision is made on whether to send the processed wafer to the next step and continue processing the remaining wafers, whether to perform a visual inspection before sending the wafer to the next step, or whether to stop processing and perform cleaning (maintenance) of the processing chamber.

In this case, the sizes and quantity of the detected particles are compared with predetermined reference values (particle management references) to determine the next operation to be performed.

Next, an example of a method for calculating these reference values (particle management references) according to this embodiment will be described. As already described, the adhesion of particles on the wafer does not mean that all of these particles will lead to killer defects. The possibility that an adhered particle will lead to a killer defect can be determined by calculations based on the relationship between the numerical aperture of the pattern, pattern density, circuit pattern width, and the like, and the sizes and quantity of the adhered particles. By performing prior testing to determine the correlation between the sizes and quantity of the particles detected during the etching operation and the sizes and quantity of the particles adhered to the wafer, the probability that particles detected during etching will lead to killer defects can be determined.

The reference values (particle management references) are determined based on values obtained using these means. The following is an example of how reference values are set up in this embodiment.

A reference value 1 is set so that if the number of detected particles having a size no less than a certain size is less than the reference value 1, the probability of a killer defect is very low (e.g., a killer defect generation probability of no more than 1%). For example, the reference value 1 can be set to 10 for particle diameters of at least 0.4 microns.

A reference value 2 is set so that if the number of detected particles having a size no less than a certain size is at or greater than the reference value 1 and less than the reference value 2, then the possibility of a killer defect is a concern (e.g., a killer defect generation probability of no more than 5%). For example, the reference value 2 can be set to 30 for particle diameters of at least 0.4 microns.

If the detected particles having a size no less than a certain size and a quantity at or greater than the reference value 2, multiple killer defects may be generated (e.g., a killer defect generation probability of 5% or higher).

Based on these reference values, if the number of particles detected during etching that have a size no less than a certain size is less than the reference value 1, the probability that a killer defect is generated is low, so the next wafer can be processed.

If the number of particles detected during etching that have a size no less than a certain size is at least the reference value 1 but less than the reference value 2, a visual inspection is performed after the etching operation is completed. If no killer defects are found as a result of the visual inspection, the wafer is sent to the following ashing step 1007. If the visual inspection results in a killer defect being found, the killer defect is evaluated to see if it is a recoverable defect or not. If this evaluation indicates that the defect is recoverable (e.g., use of the recovered circuit), the wafer is sent to the next ashing step 1007. If this evaluation determines that the defect is not recoverable, the defect position is recorded and the wafer is sent to the next ashing step 1007. Then, when the individual chips are being cut out by dicing, for example, the chip containing the unrecoverable defect is thrown out.

If the number of particles detected during etching that have a size no less than a certain size is greater than the reference value 2, the wafer which is to undergo further processing is likely to generate a large number of killer defects. Thus, a display on the monitor or an alarm is used to notify the operator of the etching apparatus so that the etching operation is stopped and cleaning (maintenance) is carried out in the plasma processing chamber.

With etching processing apparatus not equipped with a apparatus for measuring particles suspended in plasma, cleaning of the processing chamber is not necessarily carried out at appropriate times. Thus, cleaning may be performed at times when there is no need, thus reducing the availability of the apparatus. Conversely, the apparatus may continue processing even though the time to perform cleaning has passed, thus generating large numbers of defects and reducing yield.

There is also a method for determining cleaning times by using a dummy wafer beforehand to check for particles in the processing chamber. This inserts an extra operation in the series of production steps and reduces throughput while adding the cost of the dummy wafers. As the diameter of wafers increase, the cost of dummy wafers will necessarily increase. Also, the need to reduce preparatory operations using dummy wafers to check for particles in the processing chamber has been a significant issue.

With this embodiment, wafer processing can be performed while also performing real-time monitoring of the contamination status inside the processing chamber. This allows cleaning times to be optimized and eliminates the need for preparatory operations using dummy wafers. As a result, throughput is increased and the cost of dummy wafers is eliminated. Also, products produced using the steps of this embodiment are high-quality products with a particle content no greater than a reference value. This allows highly reliable products to be produced.

In the above embodiment, an implementation for an etching processing apparatus was described. However, as noted earlier, the implementation of the present invention is not limited to this. For example, the present invention can be implemented for ashing apparatus and film forming apparatus to allow real-time monitoring of particles in ashing apparatus and film forming apparatus. This can reduce defects occurring in film forming steps and ashing steps within photolithography operations, thus preventing defects and improving yield.

Eighth Embodiment

Figure 24:
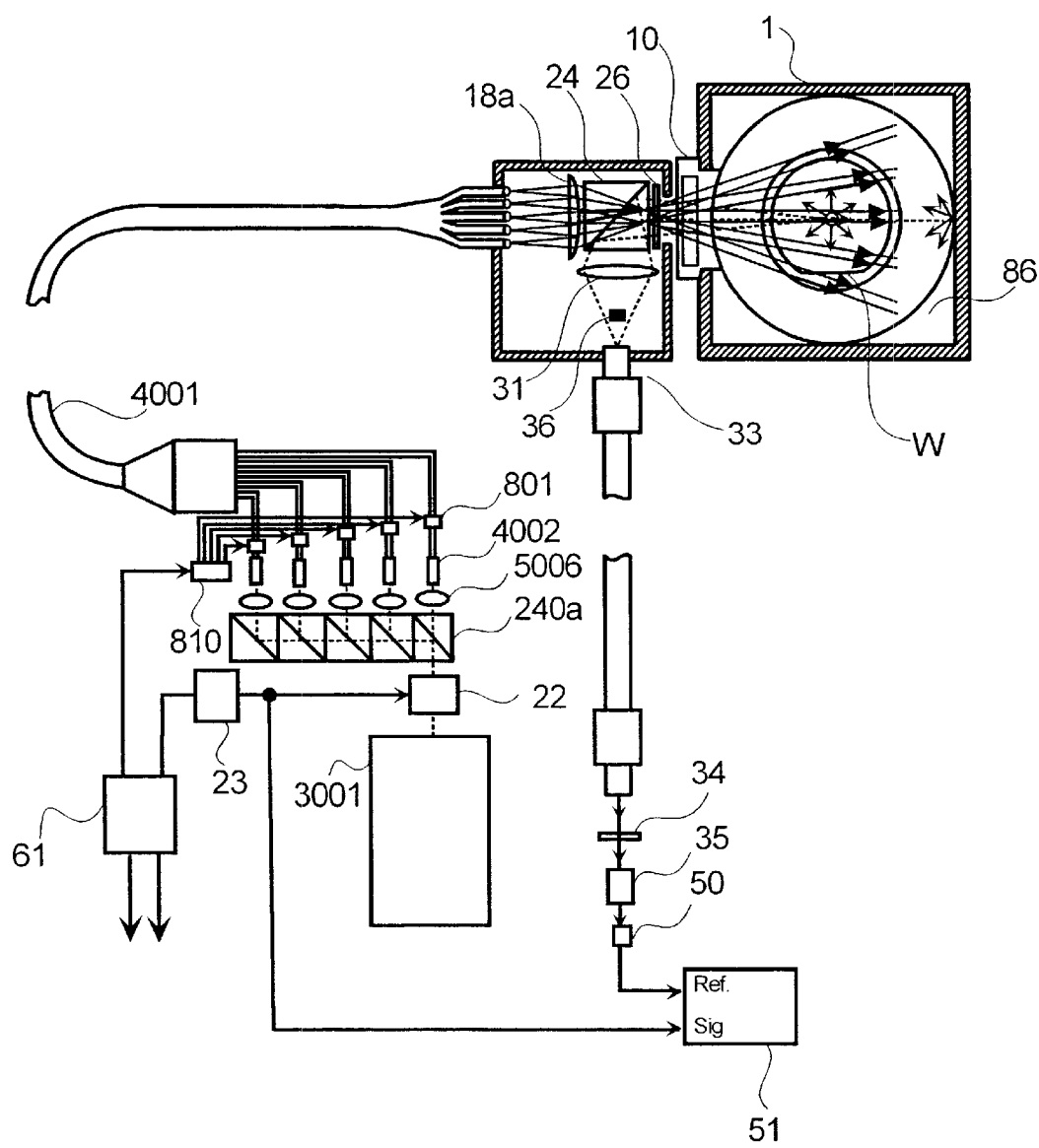
FIG. 24 is a drawing showing the architecture of an etching processing apparatus equipped with a apparatus for measuring particles suspended in plasma according to an eighth embodiment of the present invention.

Next, a plasma etching apparatus according to an eighth embodiment of the present invention will be described using FIG. 24. A laser beam is split up after being intensity modulated by an AO modulator. These beams are joined in polarization plane retention fibers, which are arranged as an array so that the polarization directions are lined up at the exit planes. The output from these polarization plane retention fibers is guided to the laser illumination/scattered light detection optical system 2003. The etching processing apparatus equipped with a apparatus for measuring particles floating in plasma has an architecture and performance similar to that of the first embodiment described above, so the corresponding description will be omitted.

A laser beam from the laser light source 3001 (e.g., a solid-state laser with a wavelength of 532 nm and an output of about 500 mW) enters the AO modulator 22. The oscillator 23 uses a frequency set up in and output from the computer 61 to apply a signal, preferably a 50% cycle duty square-wave signal, to the AO modulator 22 to perform intensity modulation at that frequency. The frequency setting here should be set up appropriately according to the frequency of the high-frequency voltage applied to the electrodes in the etching processing apparatus.

Next, a beam splitter splits the laser beam into five beams. In this embodiment, the number of split beams is five. However, this number is not restricted to five and any number can be used.

Each of the polarization plane retention fibers described above are joined to an optical fiber switch 801. This optical fiber switch is controlled by an optical fiber switch controller 810 connected to the computer 61. The split beams are guided to the laser illumination/scattered light detection optical system 2003. In this embodiment, the laser beams exiting from the polarization plane retention fibers are P-polarized. The intensity-modulated P-polarized beams exiting from the exit planes are projected by a lens 18a to different points on the wafer W. The laser beams passing through the lens 18a pass through the polarizing beam splitter 24 at a low loss. After being converted to circularly polarized beams 103 by a quarter-wave plate 26, the beams pass through the observation window 10 disposed on a side surface of the plasma processing chamber 86 and are guided into the processing chamber. The optical fiber switch controller 810 connected to the computer 61 sequentially sends in beams from the polarization plane retention fibers so that multiple points along a plane roughly parallel to the wafer surface can be illuminated. This allows illumination (particle detection) over a wide area directly over the wafer.

The circularly polarized beam 103 guided into the plasma processing chamber 86 is scattered by a suspended particle 72 in the plasma. Back-scattered light, which is the component of the particle-scattered light that propagates along the same optical axis as the circularly polarized beam 103, passes through the observation window 10 and extends to the polarizing beam splitter 24. The circularly polarized component of the back-scattered light, which corresponds to the directly reflected component, passes through the quarter-wave plate 26 again to form S-polarized light. This is reflected at a low loss by the polarizing beam splitter 24 and is focused on the entry plane of the particle-scattered light detection optical fiber 33 by a focusing lens 31.

As shown in FIG. 6, the wafer center 73b and the entry plane of the detection optical fiber 33 are in a focal relationship, but the light-receiving area of the entry end is large enough to allow detection of de-focused light scattered from the ends 73a, 73c of the wafer. As a result, particle-scattered light from the front of the wafer to the back can be detected at roughly the same sensitivity. To provide a large light-receiving plane, the method shown in FIG. 8 of using a fiber bundle is effective. The scattered light generated by an inner wall 5 of the processing chamber is focused in front of the light-receiving plane of the particle-scattered light detection optical fiber 33, so a spatial filter 36 is disposed at the focal position to block the light. The exit end of the particle-scattered light detection optical fiber 33 is connected to a spectroscope 34 formed from a monochrometer or interference filter set up for the wavelength of the polarized laser light 5008. This separates the wavelength component of the particle-scattered light from the plasma light. Then, opto-electric conversion is performed by an opto-electric converter 35.

The opto-electrically converted detection signal is amplified by an amp 50. A lock-in amp 51 performs synchronized detection using a signal output from the oscillator 23 used for intensity modulation of the laser light. The reference signal is a square-wave signal with the intensity modulation frequency described above and a duty cycle of 50%. The particle-scattered light component having the intensity modulation frequency is extracted from this detection signal. Subsequent apparatus elements and functions used to perform signal processing and evaluate particle generation status are similar to what was described for the first embodiment so the corresponding drawings and descriptions will be omitted.

In addition to the advantages from the first embodiment through the seventh embodiment, this embodiment described above allows the beam scanning module, e.g., galvano-mirrors, to be eliminated. Thus, a apparatus for measuring particles floating in plasma can be provided that is more compact than the measuring apparatus from the first embodiment through the sixth embodiment.

Ninth Embodiment

Figure 25:
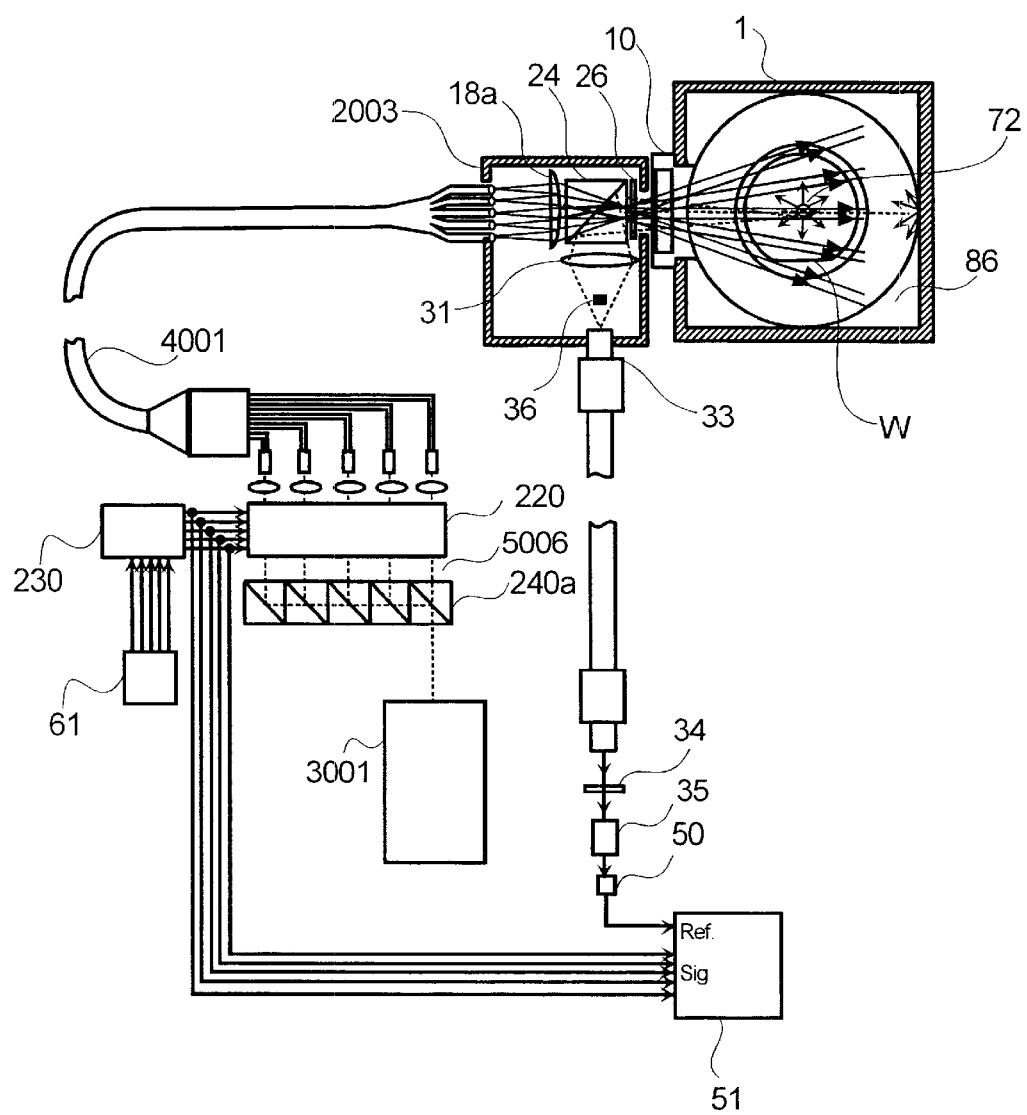
FIG. 25 is a drawing showing the architecture of an etching processing apparatus equipped with a apparatus for measuring particles suspended in plasma according to an ninth embodiment of the present invention.

Next, a plasma etching apparatus according to a ninth embodiment of the present invention will be described using FIG. 25. In this embodiment, a laser beam is split up, and each of the beams is intensity modulated by the multi-channel AO modulator 220 to provide intensity modulation. These beams are joined in polarization plane retention fibers, which are arranged as an array so that the polarization directions are lined up at the exit planes. The output from these polarization plane retention fibers is guided to a laser illumination/scattered light detection optical system 2004 [?2003?]. The etching processing apparatus equipped with a apparatus for measuring particles floating in plasma has an architecture and performance similar to that of the first embodiment described above, so the corresponding description will be omitted.

A laser beam from the laser light source 3001 (e.g., a solid-state laser with a wavelength of 532 nm and an output of about 500 mW) is split into five beams using a beam splitter 240a. In this embodiment, the number of split beams is five. However, this number is not restricted to five and any number can be used. Next, the multi-channel AO modulator 220 intensity modulates the beams at frequencies set up in the computer 61. Intensity modulation is performed preferably by applying a square-wave signal with a 50% duty cycle. These frequencies are set appropriately, taking into account the frequency of the high-frequency voltage applied to the electrodes of the etching processing apparatus. The split beams are guided to the laser illumination/scattered light detection optical system 2003.

In this embodiment, the laser beams exiting from the polarization plane retention fibers are P-polarized. The intensity-modulated P-polarized beams exiting from the exit planes are projected by a lens 18a to different points on the wafer W. The laser beams passing through the lens 18a pass through the polarizing beam splitter 24 at a low loss. After being converted to circularly polarized beams 103 by a quarter-wave plate 26, the beams pass through the observation window 10 disposed on a side surface of the plasma processing chamber 86 and are guided into the processing chamber. The optical fiber switch controller 810 connected to the computer 61 sequentially sends in beams from the polarization plane retention fibers so that multiple points along a plane roughly parallel to the wafer surface can be illuminated. This allows illumination (particle detection) over a wide area directly over the wafer.

The circularly polarized beam 103 guided into the plasma processing chamber 86 is scattered by a suspended particle 72 in the plasma. Back-scattered light, which is the component of the particle-scattered light that propagates along the same optical axis as the circularly polarized beam 103, passes through the observation window 10 and extends to the polarizing beam splitter 24. The circularly polarized component of the back-scattered light, which corresponds to the directly reflected component, passes through the quarter-wave plate 26 again to form S-polarized light. This is reflected at a low loss by the polarizing beam splitter 24 and is focused on the entry plane of the particle-scattered light detection optical fiber 33 by the focusing lens 31. As shown in FIG. 6, the wafer center 73b and the entry plane of the detection optical fiber 33 are in a focal relationship, but the light-receiving area of the entry end is large enough to allow detection of de-focused light scattered from the ends 73a, 73c of the wafer. As a result, particle-scattered light from the front of the wafer to the back can be detected at roughly the same sensitivity.

Figure 2:
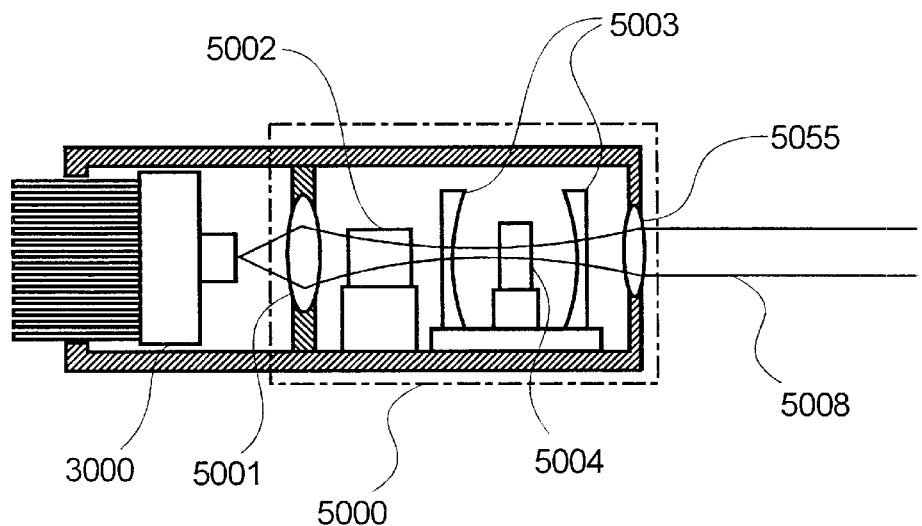
FIG. 2 is a drawing showing a standard architecture of a solid-state laser with semiconductor laser excitation according to a first embodiment of the present invention.
Figure 3:
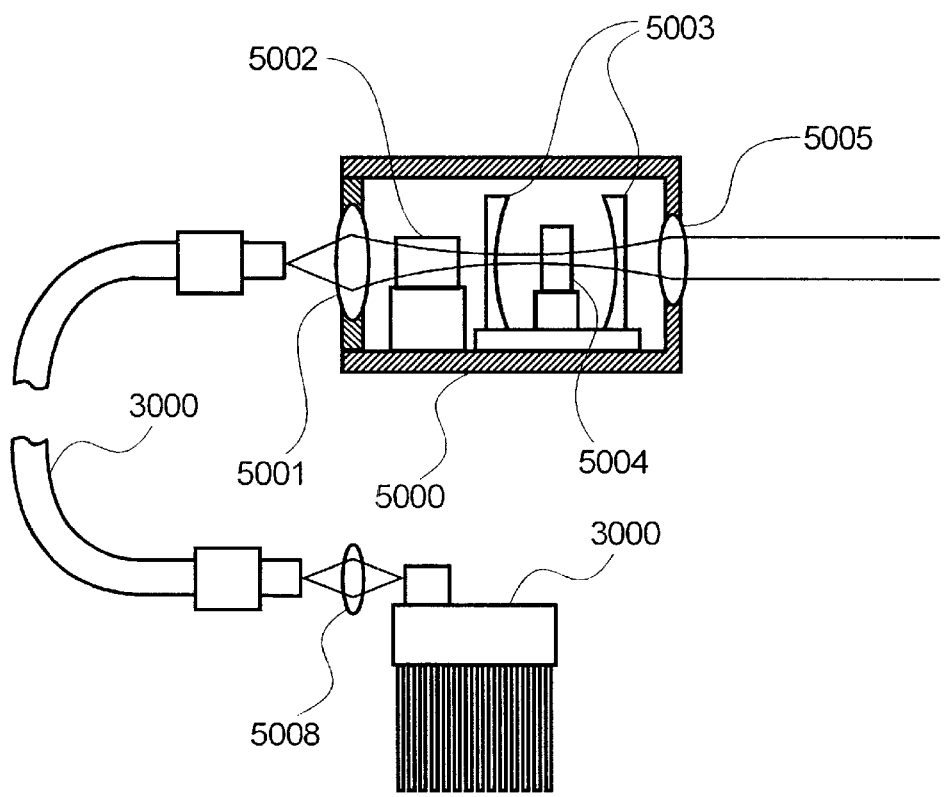
FIG. 3 is a drawing showing the architecture of a solid-state laser with external laser excitation, in which the excitation light source and the wavelength converter are separated according to a first embodiment of the present invention.

To provide a large light-receiving plane, the method shown in FIG. 2 of using a fiber bundle is effective. The scattered light generated by an inner wall 5 of the processing chamber is focused in front of the light-receiving plane of the particle-scattered light detection optical fiber 33, so the spatial filter 36 is disposed at the focal position to block the light. The exit end of the particle-scattered light detection optical fiber 33 is connected to a spectroscope 34 formed from a monochrometer or interference filter set up for the wavelength of the polarized laser light 5008. This separates the wavelength component of the particle-scattered light from the plasma light. Then, opto-electric conversion is performed by the opto-electric converter 35. The opto-electrically converted detection signal is amplified by the amp 50. The lock-in amp 51 performs synchronized detection using a signal output from the oscillator 23 used for intensity modulation of the laser light. The reference signal is a square-wave signal with the intensity modulation frequency described above and a duty cycle of 50%. The particle-scattered light component having the intensity modulation frequency is extracted from this detection signal.

The difference between this embodiment and the eighth embodiment described above is that the laser beams from the polarization plane retention fibers are intensity modulated at different frequencies. By performing synchronized detections of these frequencies used for intensity modulation from the light scattered from particles, the laser lights from the polarization plane retention fibers described above can be distinguished from each other during detection. Thus, particle detection can be performed simultaneously for multiple points above the wafer W, and particle positions can be identified.

The subsequent apparatus architecture and functions provided for signal processing and evaluating contamination generation are similar to the first embodiment described above, so their descriptions will be omitted.

This embodiment as described above can provide the advantages of the eighth embodiment. In addition, particle detection can be performed simultaneously for multiple points above the wafer W, and particle positions can be identified.

Tenth Embodiment

Figure 26:
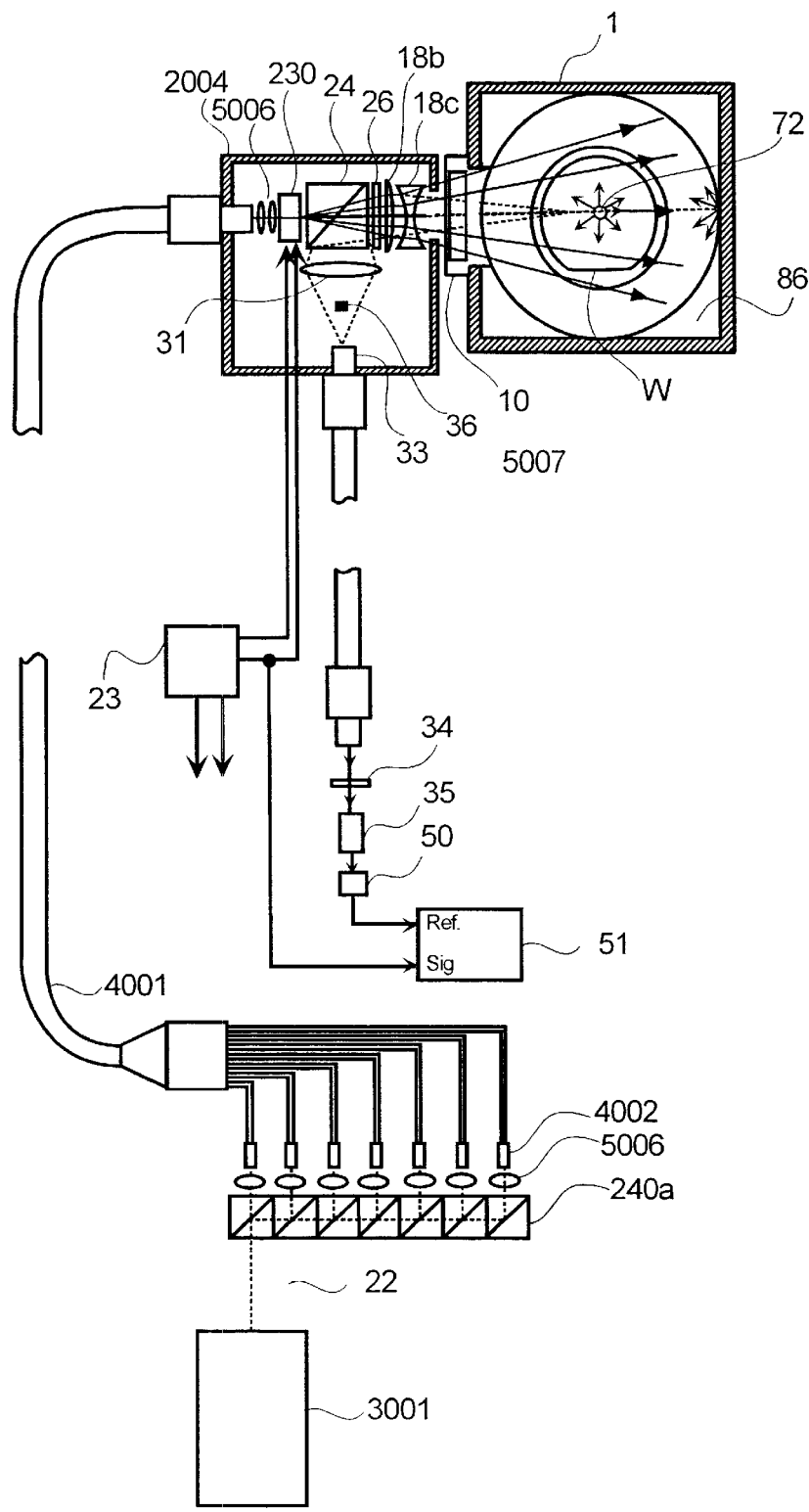
FIG. 26 is a drawing showing the architecture of an etching processing apparatus equipped with a apparatus for measuring particles suspended in plasma according to an tenth embodiment of the present invention.
Figure 27:
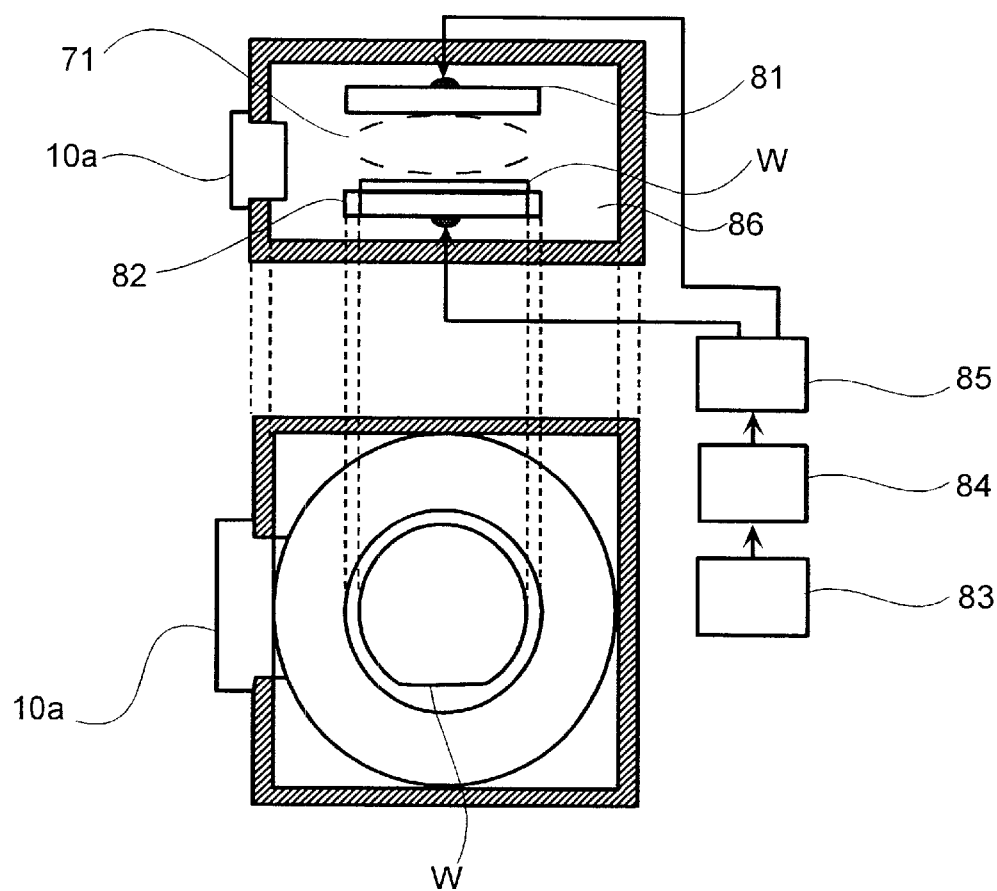
FIG. 27 is a drawing showing a flat-plate plasma etching apparatus.

A plasma etching apparatus according to a tenth embodiment of the present invention will be described using FIG. 26. In this embodiment, an AO deflector integrates intensity modulation and beam scanning operations. The etching processing apparatus equipped with a apparatus for measuring particles floating in plasma has an architecture and performance similar to that of the first embodiment described above, so the corresponding description will be omitted.

First, as in the eighth embodiment, a laser beam from the illumination laser light source is split into multiple beams, and the split beams are joined to a polarization plane retention fiber 4001. In the polarization plane retention fiber 4001, the fibers are bundled so that the polarization directions of the exit planes of the fibers are the same. The polarized laser light from the bundled polarization plane retention fiber 4001 is guided to the laser illumination/scattered light detection optical system 2004. The difference between this and the eighth embodiment is that intensity modulation is not performed using an AO modulator. Other aspects of the architecture are identical to those of the eight embodiment so the corresponding descriptions will be omitted.

The polarization plane retention fiber 4001 guides the laser light to the laser illumination/scattered light detection optical system 2004. In this embodiment, the laser beam exiting from the polarization plane retention fiber 4001 is P-polarized. The laser light entering the laser illumination/scattered light detection optical system 2004 is expanded using a beam expander 5006 and guided to the AO deflector 230. The AO deflector 230 performs intensity modulation at specific frequencies by applying a square-wave signal, preferably with a 50% duty cycle, using frequencies set up in and output from the computer 61. The frequency settings are set appropriately taking into account the frequency of the high-frequency voltage applied to the electrodes of the etching processing apparatus. The AO deflector 230 also controls deflection angles for diffracted light based on signals from the computer 61 so that beam scanning is performed. The P-polarized, intensity-modulated scanning beam passes through the polarizing beam splitter 24 at a low loss, and is converted to a circularly polarized beam 103 by the quarter-wave plate 26. A short-focus lens 18b and a concave lens 18c guide the scanning beam through the observation window disposed on a side surface of the plasma processing chamber 86 so that scanning takes place over a wide area above the wafer W.

The circularly polarized beam 103 guided into the plasma processing chamber 86 is scattered by a suspended particle 72 in the plasma. Back-scattered light, which is the component of the particle-scattered light that propagates along the same optical axis as the circularly polarized beam 103, passes through the observation window 10, and goes toward the polarizing beam splitter 24. The circularly polarized component of the back-scattered light, which corresponds to the directly reflected component, passes through the quarter-wave plate 26 again to form S-polarized light. This is reflected at a low loss by the polarizing beam splitter 24 and is focused on the entry plane of the particle-scattered light detection optical fiber 33 by a focusing lens 31.

As shown in FIG. 6, the wafer center 73b and the entry plane of the detection optical fiber 33 are in a focal relationship, but the light-receiving area of the entry end is large enough to allow detection of de-focused light scattered from the ends 73a, 73c of the wafer. As a result, particle-scattered light from the front of the wafer to the back can be detected at roughly the same sensitivity. To provide a large light-receiving plane, the method shown in FIG. 8 of using a fiber bundle is effective. The scattered light generated by an inner wall 5 of the processing chamber is focused in front of the light-receiving plane of the particle-scattered light detection optical fiber 33, so a spatial filter 36 is disposed at the focal position to block the light. The exit end of the particle-scattered light detection optical fiber 33 is connected to a spectroscope 34 formed from a monochrometer or interference filter set up for the wavelength of the polarized laser light 5008. This separates the wavelength component of the particle-scattered light from the plasma light. Then, opto-electric conversion is performed by an opto-electric converter 35. The opto-electrically converted detection signal is amplified by an amp 50. A lock-in amp 51 performs synchronized detection using a signal output from the oscillator 23 used for intensity modulation of the laser light. The reference signal is a square-wave signal with a frequency of 170 kHz and a duty cycle of 50%. The particle-scattered light component having that frequency is extracted from this detection signal.

The subsequent apparatus architecture and functions provided for signal processing and evaluating contamination generation are similar to the first embodiment described above, so their descriptions will be omitted.

In the present invention as described above, detection is performed for back-scattered light. This allows the laser illumination/scattered light detection optical systems to be formed as a single unit that can be used with processing apparatus that only have a single observation window. In addition, adjustment of optical axes and the like is easier compared to structures in which the illumination optical system and the detection optical system are formed separately, thus allowing the optical system as a whole to be more compact.

Also, the excitation light source, which is the element in the illumination light source that is the biggest heat source and that requires a large heat-dissipating heat sink, is separated from the laser illumination/scattered light detection optical system. As a result, the optical system as a whole can be made even more compact.

Also, compared to other elements in the plasma-suspended particle measuring apparatus, the excitation light source has a relatively short lifespan and can be expected to have a high frequency of being replaced. By separating this excitation light source from the laser illumination/scattered light detection optical system in the present invention, the excitation light source can be replaced directly without having to manipulate the laser illumination/scattered light detection optical system. This improves maintenance efficiency and reduces the downtime of the apparatus.

Also, according to the present invention, laser scanning is performed without using galvano-mirrors, which can be expected to have a relatively short lifespan and a high frequency of being replaced compared to other elements in a plasma-suspended particle measuring apparatus. Thus, the need to replace galvano-mirrors when they malfunction is eliminated, and the optical system can be made more compact.

Also, in this invention, weak particle-scattered light can be separated by wavelength and frequency from plasma emissions, which obstruct the detection of particles in plasma. Thus, compared to conventional methods that only separate by wavelength, the detection sensitivity for particles suspended in plasma can be improved significantly. With the conventional method using wavelength separation only, the minimum detection sensitivity was a diameter of about 1 micron. However, with the method of the present invention, the minimum detection sensitivity can be improved to a diameter of about 0.2 microns, thus allowing stable particle detection for the entire wafer surface.

Also, since this embodiment uses detection of back-scattered light, the illumination beam can be rotationally scanned horizontally, thus allowing the two-dimensional distribution of particles to be easily known.

Also, this invention performs particle detection for the entire wafer surface and is able to determine the number, size, and distribution of particles. Thus, the operator can check this information in real time, e.g., through a display.

Since the present invention allows real-time evaluation of the contamination status within the processing chamber based on the determined number, size, and distribution of particles, it would be possible, for example, to optimize the cleaning schedule and improve the operating efficiency of the apparatus. Also, clustered defects (large numbers of defects being generated all at once) can be prevented, leading to improved yield. Also, since processing proceeds while the contamination status in the processing chamber is continuously monitored, the semiconductor substrates and liquid crystal substrates produced in this manner will be produced in an environment that does not contain more than a predetermined level of particles, thus providing products with high quality and reliability.

Also, this embodiment can reduce the frequency of evaluations of processing chamber contamination using dummy wafers and contamination status evaluations via random inspections. Thus, the costs involved in the use of dummy wafers can be reduced.

These advantages allow the contamination status inside the etching apparatus processing chamber to be monitored in real time. As a result, wafer defects resulting from adhered particles can be reduced so that high-quality semiconductor elements can be produced, and the timing at which the apparatus should be cleaned can be determined accurately.

Also, the frequency of pre-checking operations using dummy wafers can be reduced, thus reducing costs and improving production efficiency. This also allows automation of the production line.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. A method for detecting particles suspended in a plasma processing apparatus comprising the following steps:

illuminating the inside of said plasma processing apparatus with a plurality of laser beams from an observation window of said plasma processing apparatus when plasma processing is being performed on a semiconductor device in said plasma processing apparatus;

separating and detecting, via said observation window, light reflected inside said plasma processing apparatus due to said illumination from light reflected from inner wall surfaces of said plasma processing apparatus; and obtaining information about particles suspended in said plasma processing chamber by processing said detected signal.

2. A method for detecting particles suspended in a plasma processing apparatus as described in claim 1 wherein said plurality of laser beams illuminating the inside of said plasma processing apparatus from an observation window is emitted from a laser light source and transported via an optical fiber.

3. A method for detecting particles suspended in a plasma processing apparatus as described in claim 1 wherein said plurality of laser beams illuminating the inside of said plasma processing apparatus from an observation window is sequentially switched to provide illumination.

4. A method for detecting particles suspended in a plasma processing apparatus as described in claim 1 wherein said plurality of laser beams illuminating the inside of said plasma processing apparatus from an observation window is intensity modulated.

5. A apparatus for detecting particles suspended inside a plasma processing chamber comprising:

a laser light source;

means for separating a laser beam emitted from said laser light source into a plurality of beams;

first optical fiber means transferring said plurality of laser beams separated by said separating means;

means for laser beam illumination illuminating the inside of a plasma processing apparatus by way of an observation window of said plasma processing apparatus using said plurality of laser beams transferred by said first optical fiber means;

means for focusing, via said observation window, light projected by said laser beam illuminating means and reflected in said plasma processing chamber;

second optical fiber means transferring reflected light focused by said focusing means; and means for processing signals detecting said reflected light transferred by said second optical fiber means and obtaining information about particles suspended in said plasma processing apparatus.

6. A apparatus for detecting particles suspended inside a plasma processing chamber as described in claim 5 further comprising means for switching sequentially switching said plurality of laser beams; wherein:

said laser beam illuminating means illuminates the inside of said plasma processing chamber by sequentially switching said plurality of laser beams.

7. A apparatus for detecting particles suspended inside a plasma processing chamber as described in claim 5 wherein said focusing means performs focusing on light reflected in said plasma processing chamber while blocking light reflected from inner wall surfaces of said plasma processing chamber.

8. A semiconductor device processing apparatus comprising:

means for processing plasma equipped with an internal table for mounting a substrate to be processed and at least one observation window;

a laser light source emitting a plurality of laser beams;

first optical fiber means transferring a plurality of laser beams emitted from said laser light source;

laser beam illuminating means attached to said observation window and providing illumination, via said observation window, above and roughly parallel to said table in said plasma processing means using said plurality of laser beams transferred by said first optical fiber means;

means for focusing light from said laser beam illuminating means reflected inside said plasma processing means;

second optical fiber means transferring light focused by said focusing means;

means for detecting particles suspended in said plasma processing apparatus by detecting light transferred by said second optical fiber means; and means for outputting information relating to particles suspended in said plasma processing means detected by said detecting means.

9. A semiconductor device processing apparatus as described in claim 8 wherein:

said laser light source is equipped with a switching module that emits said plurality of laser beams in a sequentially switching manner; and said laser beam illuminating means sequentially illuminates the inside of said plasma processing means using a plurality of sequentially switched laser beams from said laser light source.

10. A semiconductor device processing apparatus as described in claim 8 wherein:

said laser light source is equipped with an intensity modulation module modulating intensities of said plurality of laser beams;

said laser beam illuminating means illuminates the inside of said plasma processing means using a plurality of laser beams intensity modulated by said laser light source.

11. A semiconductor device processing apparatus as described in claim 8 wherein said focusing means focuses, via said observation window, light from said laser beam illuminating means reflected inside said plasma processing means.

12. A semiconductor device processing apparatus as described in claim 8 wherein said focusing means focuses light from said laser beam illuminating means reflected inside said plasma processing means while blocking light reflected from wall surfaces of said plasma processing means.

* * * * *